(12) United States Patent
Shen et al.

(10) Patent No.: US 7,435,701 B2
(45) Date of Patent: Oct. 14, 2008

(54) CATALYTIC COMPOSITION AND ITS PREPARATION AND USE FOR PREPARING POLYMERS FROM ETHYLENICALLY UNSATURATED MONOMERS

(75) Inventors: Han Shen, Lower Gwynedd, PA (US); Brian Leslie Goodall, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 60 days.

(21) Appl. No.: 11/418,676

(22) Filed: May 4, 2006

(65) Prior Publication Data

US 2006/0270811 A1 Nov. 30, 2006

Related U.S. Application Data

(60) Provisional application No. 60/685,473, filed on May 27, 2005.

(51) Int. Cl.
*B01J 31/22* (2006.01)
*C08F 4/70* (2006.01)

(52) U.S. Cl. .................. 502/113; 502/152; 502/162; 502/167; 526/115; 526/161; 526/165

(58) Field of Classification Search ................. 502/113, 502/150, 162, 152, 167; 526/115, 165, 161
See application file for complete search history.

(56) References Cited

U.S. PATENT DOCUMENTS

| | | | |
|---|---|---|---|
| 3,454,538 | A | 7/1969 | Naarmann |
| 3,501,415 | A | 3/1970 | Herwig et al. |
| 4,906,754 | A | 3/1990 | Klabunde et al. |
| 6,005,151 | A | 12/1999 | Hermann et al. |
| 6,544,919 | B1 | 4/2003 | Tagge et al. |
| 6,613,915 | B1 | 9/2003 | Johnson et al. |
| 6,737,483 | B1 | 5/2004 | Tomov et al. |
| 6,864,210 | B2 * | 3/2005 | Hlatky et al. ................ 502/150 |
| 7,078,363 | B2 | 7/2006 | Claverie et al. |
| 2002/0120160 | A1 | 8/2002 | Makoto |
| 2004/0063574 | A1 | 4/2004 | Theopold |

FOREIGN PATENT DOCUMENTS

| | | |
|---|---|---|
| EP | 1 508 577 | 2/2005 |
| EP | 1 607 413 | 12/2005 |
| EP | 1 607 414 | 12/2005 |
| WO | WO 99/474474 A | 9/1999 |
| WO | WO 03/102038 A | 12/2003 |
| WO | WO 03/102038 A1 | 12/2003 |
| WO | WO 2005/012315 | 2/2005 |

OTHER PUBLICATIONS

Younkin, T. R., "Neutral, Single-Component Nickel . . . " Science, American Association for the Advancement of Science, New York, US, vol. 287, 2000, pp. 460-462.
Pickel, M., "Facile Preparation of Activation of High-Productivity . . . " Helvetica Chimica Acta, Verlag Helvetica Chimica Acta. Basel, CH, vol. 85, Dec. 2002, p. 4337-4352.
Macadams, L A, "The (PH) 2NACNAC Ligand in Organochromium Chemistry" Organometallics, ACS, Washington, DC, US. vol. 21, No. 5, Mar. 4, 2002, pp. 952-960.
Gibson, V C, "Chromium (III) Complexes Bearing N, . . . " Chemical Communications, Royal Society of Chemistry, GB, 1998, pp. 1651-1652.
Shapiro, E. A., "Stereospecific Catalytic Dimerization of the Methyl Ester of . . . " Chemical Abstract Service, Columbus, Ohio, data accession No. 1988: 130985.
Musuoglu, Emel, "Synthesis and Complexation of the a New Branched Vic-dioxime" Chemical Abstracts Service, Database accession No. 1997: 137259.
Britovsek, G. J. P., "Cationic Methyl-Palladium(II) Complexes . . . " Jounal of Organometallic Chemistry, Elsevier-Sequoia S.A.
Sennami, Hirotaka et al., "Preparation of Porphyrin Dimers" Chemical Abstracts Service, Columbus, Ohio. Database accession No. 1998: 76249.
Bilgin-Eran, Belkiz et al, "Synthesis and Mesomorphism of Fluroalkylated Organometallic Mesogens" Journal of Materials Chemistry, 16(12), Nov. 23, 2005, p. 1137, and p. 1143.
Kleijn, Henk et al, "2-(1-(Dimethylamino)ethyl)phenylpalladium (II) . . . " Inorganica Chimica Acta, 359(9), Dec. 19, 2005, p. 2678 compounds 2A-2C.
Hope, Eric G. et al: "Platinum Group Metal Complexes . . . ", Journal of the Chemical Society, Dalton Translations: Inorganic Chemistry, (22), 1998. p. 3766-3768.
Gok, Yaser et al: "Axial-ligation and Macrocyclization of Novel . . . " Transition Metal Chemistry (London) 20(3) pp. 235-237.
Trush, Elizaveta, A. et al: "Metal Carbacylamidophosphates: . . . " Polyhedron 22(9), Apr. 4, 2003, p. 1222-p. 1224, and p. 1227.
Lahuerta, Pascual et al: "Novel Unsymmetrical Ortho-Metalated . . . " Tetrahedron Letters, 40(9), 1999, p. 1752.
Buchowicz, Wlodzimierz et al: "Novel Ruthenium(II)2 Carboxylates . . . " Chemistry-A European Journal, 7(13) pp. 2842-2843 and pp. 2845-2846.
Thetiot, Franck et al: "Discrete Dinuclear complexes and two dimensional . . . " European Journal of Inorganic Chemistry, (19) 2004, pp. 3786 and 3789-3790.
Wong, Richard C. S. et al: "A Facile Reaction of Bibenzyl Trisulfide . . . " Inorganica Chimica Acta, 358(4) Oct. 28, 2004 p. 1270 and p. 1272.
Weng, Zhiqang et al: "Complexes From Ring Opening of Lawesson's Reagent . . . " Organometallics, 22(8) 2003, p. 1647-1651.
Liting Li, et al., "Catalyst/Cocatalyst Nuclearity Effects in Single-Site Polymerication. Enhanced Polyethylene Branching and α-Olefin Comonomer Enchainment in Polymerizations Mediated by Binuclear Catalysts and Cocatalysts via a New Enchainment Pathway," *Journal of American Chemical Society*, 2002, 1272-12741, vol. 123, No. 43.
Hongbo Li, et al., "Catalyst/Cocatalyst Nuclearity Effects in Single-Site Olefin Polymerization. Significantly Enhanced 1-Octene and Isobutene Comonomer Enchainment in Ethylene Polymerizations Mediated by Binuclear Catalysts and Cocatalysts," *Journal of American Chemical Society*, 2003, 10788-10789, vol. 125, No. 36.

* cited by examiner

*Primary Examiner*—Caixia Lu
(74) *Attorney, Agent, or Firm*—Richard R. Clikeman; Thomas S. Deibert

(57) ABSTRACT

A catalytic composition, including a neutral metal-pair complex, is disclosed, along with a method for its preparation. A method for the polymerization of ethylenically unsaturated monomers using the catalytic composition, and the addition polymers produced thereby are also disclosed.

10 Claims, No Drawings

CATALYTIC COMPOSITION AND ITS PREPARATION AND USE FOR PREPARING POLYMERS FROM ETHYLENICALLY UNSATURATED MONOMERS

CROSS REFERENCE TO RELATED PATENT APPLICATIONS

This is a non-provisional application of prior U.S. Provisional Application Ser. No. 60/685,473 filed on May. 27, 2005.

The present invention relates to a catalytic composition and a method of preparing that catalytic composition. The present invention further relates to a method for polymerizing ethylenically unsaturated monomers, including non-polar olefinic monomers, polar olefinic monomers, and combinations thereof, in the presence of the catalytic composition, and to the polymers produced thereby.

Currently, the use of free radical initiators to produce polymers from combinations of non-polar olefins and polar olefins for the acrylic polymer markets gives little or no control over polymer architecture (tacticity or crystallinity, blockiness, molecular weight, and molecular weight distribution) and thus limits the accessible range of materials performance properties. Because these free radical processes require extreme pressures, they are associated with high capital investment and manufacturing costs, and, of course, increased safety hazards.

The development of neutral transition metal catalysts for polymerization of olefinic monomers started with the commercially significant Shell Higher Olefin Process (SHOP), which was largely due to the effort by Keim et al in late 1960s to early 1970s. This process utilizes a well-defined neutral nickel catalyst, such as Catalyst W, to make linear oligomeric ethylene ($C_4$-$C_{20}$), which is commonly used for detergents, plasticizers, lubricants and a variety of fine chemicals. (Keim, W.; Kowalt, F. H.; Goddard, R.; Krüger, C. *Angew. Chem., Int. Ed. Engl.* 1978, 17, 466.)

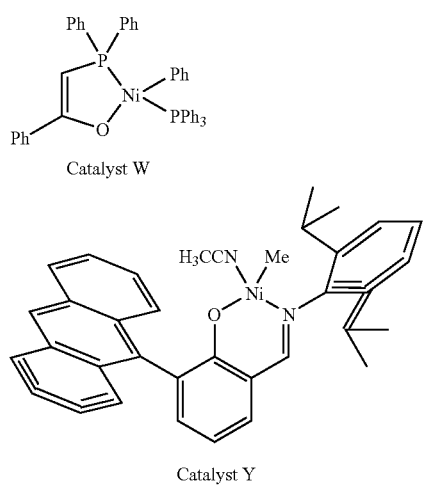

In recent years, there has been a rapidly growing interest in neutral transition metal catalysts for polymerization of olefinic monomers, because they are less oxophillic and potentially have better tolerance toward polar reaction media and polar monomers than their cationic counterparts. For example, Catalyst Y is a representative of Ni(sal) catalysts that polymerize ethylene in the presence of esters, alcohols, water, etc. However, attempts to copolymerize polar monomers (e.g. methyl acrylate) and ethylene using Ni(sal) catalysts have led only to catalyst deactivation via hydrogen transfer from acrylate to catalyst. (Waltman, A. W.; Younkin, T. R.; Grubbs, R. H. *Organometallics,* 2004, 23, 5121. and references therein)

We have surprisingly discovered a catalytic composition including a new family of neutral metal-pair complexes. These neutral metal-pair complexes are very active in the homo- and co-polymerization of ethylenically unsaturated monomers. The ethylenically unsaturated monomers polymerizable by catalysis using the catalytic composition of the present invention include non-polar olefinic monomers, polar olefinic monomers, and combinations thereof. This new family of catalytic compositions includes neutral metal-pair complexes wherein the neutral metal-pair complex includes at least one metal atom pair, and each metal of the metal atom pair has, independently, four (4), five (5), or six (6) occupied coordination sites.

One aspect of the present invention is directed to a catalytic composition comprising a catalytic composition comprising a neutral metal-pair complex, comprising a first metal atom, $M^1$, and a second metal atom, $M^2$, having a through-space internuclear distance of at least 1.5 Angstroms and no more than 20 Angstroms; wherein said neutral metal-pair complex is according to formula I,

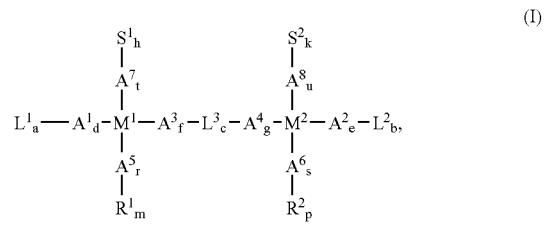

wherein:
$L^1$ is a set of first ligands;
$L^2$ is a set of second ligands;
$L^3$ is a set of bridging moieties;
$R^1$ is a set of first anionic hydrocarbyl containing radicals;
$R^2$ is a set of second anionic hydrocarbyl containing radicals;
$S^1$ is a set of first labile ligands;
$S^2$ is a set of second labile ligands;
$A^1$-$A^8$ are sets of coordination bonds;
a, b, h, k, m, and p are selected from 0 and 1;
c equals 1;
$1 \leq m+p \leq 2$;
the sum d+f+r+t=4, 5, or 6;
and the sum e+g+s+u=4, 5, or 6;
with the proviso that
(i) when the sum d+f+r+t=4,
$M^1$ is selected from nickel, palladium, copper, iron, cobalt, rhodium, chromium, and manganese; d, r, and t are selected from 0, 1, 2, and 3; and f is selected from 1, 2, 3, and 4; and
when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 5$; $1 \leq r+s \leq 5$; $0 \leq t+u \leq 5$; and $2 \leq f+g \leq 7$;
when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 6$; $1 \leq r+s \leq 6$; $0 \leq t+u \leq 6$; and $2 \leq f+g \leq 8$; or when the sum $e+g+s+u=6$, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 7$; $1 \leq r+s \leq 7$; $0 \leq t+u \leq 7$; and $2 \leq f+g \leq 9$;

(ii) when the sum $d+f+r+t=5$;

$M^1$ is selected from iron, cobalt, ruthenium, rhodium, chromium, and manganese; d, r, and t are selected from 0, 1, 2, 3, and 4; f is selected from 1, 2, 3, 4, and 5; and when the sum $e+g+s+u=4$, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 6$; $1 \leq r+s \leq 6$; $0 \leq t+u \leq 6$; and $2 \leq f+g \leq 8$;

when the sum $e+g+s+u=5$, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 7$; $1 \leq r+s \leq 7$; $0 \leq t+u \leq 7$; and $2 \leq f+g \leq 9$; or when the sum $e+g+s+u=6$, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 8$; $1 \leq r+s \leq 8$; $0 \leq t+u \leq 8$; and $2 \leq f+g \leq$; and (iii) when the sum $d+f+r+t=6$;

$M^1$ is selected from copper, iron, cobalt, ruthenium, rhodium, chromium, and manganese; d, r, and t are selected from 0, 1, 2, 3, 4, and 5; f is selected from 1, 2, 3, 4, 5, and 6; and when the sum $e+g+s+u=4$, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 7$; $1 \leq r+s \leq 7$; $0 \leq t+u \leq 7$; and $2 \leq f+g \leq 9$;

when the sum $e+g+s+u=5$, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 8$; $1 \leq r+s \leq 8$; $0 \leq t+u \leq 8$; and $2 \leq f+g \leq 10$; or when the sum $e+g+s+u=6$, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 9$; $1 \leq r+s \leq 9$; $0 \leq t+u \leq 9$; and $2 \leq f+g \leq 11$.

Another aspect of the present invention is directed to a method for preparing a neutral metal-pair complex, comprising:

(I) providing a first precursor complex according to formula II

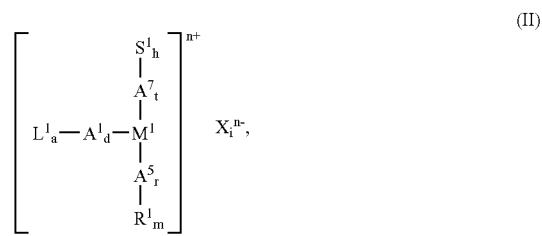

wherein:

$L^1$ is a set of first ligands;
$R^1$ is a set of first anionic hydrocarbyl containing radicals;
$S^1$ is a set of first labile ligands;
X is a set of anionic counter ions;
$A^1$, $A^5$, $A^7$ are sets of coordination bonds;
a, h, m, and i are selected from 0 and 1;
$n=0, 1, 2,$ or 3; when $n=0$, $i=0$; when $n=1, 2,$ or 3, $i=1$; and
the sum $d+r+t=4, 5,$ or 6;

with the proviso that (i) when the sum $d+r+t=4$,
$M^1$ is selected from nickel, palladium, copper, iron, cobalt, rhodium, chromium, and manganese;
d is selected from 0, 1, 2, 3, and 4; and
r and t are selected from 0, 1, 2, and 3;

(ii) when the sum $d+r+t=5$,
$M^1$ is selected from iron, cobalt, ruthenium, rhodium, chromium, and manganese;
d is selected from 0, 1, 2, 3, 4, and 5; and
r and t are selected from 0, 1, 2, 3, and 4; or (iii) when the sum $d+r+t=6$
$M^1$ is selected from copper, iron, cobalt, ruthenium, rhodium, chromium, and manganese;
d is selected from 0, 1, 2, 3, 4, 5, and 6; and
r and t are selected from 0, 1, 2, 3, 4, and 5;

(II) providing a second precursor complex according to formula III

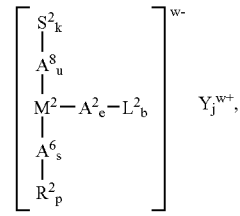

wherein:

$L^2$ is a set of second ligands;
$R^2$ is a set of second anionic hydrocarbyl containing radicals;
$S^2$ is a set of second labile ligands;
Y is a set of cationic counter ions;
$A^2$, $A^6$, $A^8$ sets of coordination bonds;
b, k, p, and j are selected from 0 and 1;
$n=0, 1, 2,$ or 3; and
the sum $e+s+u=4, 5,$ or 6;

with the proviso that (i) when the sum $e+s+u=4$,
$M^2$ is selected from nickel, palladium, copper, iron, cobalt, rhodium, chromium, and manganese;
e is selected from 0, 1, 2, 3, and 4; and
s and u are selected from 0, 1, 2, and 3;

(ii) when the sum $e+s+u=5$,
$M^2$ is selected from iron, cobalt, ruthenium, rhodium, chromium, and manganese;
e is selected from 0, 1, 2, 3, 4, and 5; and
s and u are selected from 0, 1, 2, 3, and 4; or (iii) when the sum e+s+u=6
$M^2$ is selected from copper, iron, cobalt, ruthenium, rhodium, chromium, and manganese;
e is selected from 0, 1, 2, 3, 4, 5, and 6; and
s and u are selected from 0, 1, 2, 3, 4, and 5; and
wherein: $1 \leq m+p \leq 2$; w=n; j=i; and
(III) contacting said first precursor with said second precursor to produce said neutral metal-pair complex.

A yet another aspect of the present invention is directed to a method for preparing an addition polymer comprising:
(a) combining:
(i) a catalytic composition according to claim 1; and
(ii) an ethylenically unsaturated monomer; and
(b) polymerizing said ethylenically unsaturated monomer in the presence of said catalytic composition to form said addition polymer.

Used herein, the following terms have these definitions:

"Range". Disclosures of ranges herein take the form of lower and upper limits. There may be one or more lower limits and, independently, one or more upper limits. A given range is defined by selecting one lower limit and one upper limit. The selected lower and upper limits then define the boundaries of that particular range. All ranges that can be defined in this way are inclusive and combinable, meaning that any lower limit may be combined with any upper limit to delineate a range.

A "catalytic composition" is a composition including at least one "neutral metal-pair complex", wherein the neutral metal-pair complex includes at least one "metal atom pair" (interchangeably, "metal pair". Each metal atom pair includes a single "first metal atom" represented by the symbol "$M^1$" ("metal atom $M^1$") and a single "second metal atom" represented by the symbol "$M^2$" ("metal atom $M^2$").

The "through-space internuclear metal atom pair distance" (referred to interchangeably, herein, as "through-space internuclear distance") for a metal atom pair of a neutral metal-pair complex is the distance between the nucleus of the first metal atom $M^1$ of a metal atom pair and the nucleus of the second metal atom $M^2$ of that pair. This through-space internuclear distance is equal to or less than the "through-bond internuclear distance", which is the distance traced along connecting bonds. For example, if a metal-metal bond exists between $M^1$ and $M^2$ of a metal atom pair, the through-space internuclear distance and the metal-metal through-bond distance are the same. If this metal atom pair also had a third ligand as a bridging moiety between $M^1$ and $M^2$, the distance from $M^1$ to $M^2$ along the bonds of that third ligand would be greater than the through-space distance.

The "through-space internuclear metal atom pair distance" for a metal pair of a neutral metal-pair complex may be determined using quantum chemical calculation methods known to those of ordinary skill in the art of computational chemistry. For example, a quantum chemical calculation method suitable for use with the present invention includes density functional methods such as Jaguar™ software, Version 5.0. For a given neutral metal-pair complex, one of ordinary skill in the art of computational chemistry can utilize accepted rules of chemical connectivity, the "LACVP basis set", and the "B3LYP functional" to calculate the interatomic metal-metal distance (i.e., the through-space internuclear metal atom pair distance) for a metal pair of that neutral metal-pair complex. Using Jaguar™ software, Version 5.0, the structure of the neutral metal-pair complex is geometry optimized, using as a starting point a structure having the proper atomic connectivity. The metal-metal interatomic distance for a metal pair of that complex (i.e., the "through-space internuclear metal pair distance") can then be determined from the atomic cartesian coordinates of the geometry optimized structure. Jaguar™ Verion 5.0 software and the Jaguar 5.0 Operating Manual, January 2003, are available from Schrödinger, L. L. C., 120 West $45^{th}$ Street, $32^{nd}$ Floor, New York, N.Y. 10036.

The first metal atom and the second metal atom of a metal atom pair may further exhibit "cooperativity" during the polymerization of ethylenically unsaturated monomers, wherein cooperativity means that the first metal atom will positively influence the ability of the second metal atom to polymerize ethylenically unsaturated monomer, or the second metal atom will positively influence the ability of the first metal atom to polymerize ethylenically unsaturated monomer, or both. Not wishing to be bound by any particular theory, it is thought that, when the two metals of a metal atom pair exhibit cooperativity, that cooperativity may, for example, take the form wherein a metal of the pair favorably modifies the electronic, steric, or other spatial environment of the other metal of the pair, or of the inserting ethylenically unsaturated monomer, or of the portion of any polymer chain growing from, or otherwise associated with, the metal atom pair. In certain embodiments, a single ethylenically unsaturated monomer may become attached to, or otherwise associated with, each of the members of a metal atom pair, either sequentially or simultaneously, during its incorporation into a polymer by insertion polymerization catalyzed by that metal atom pair.

A "coordination bond" can be a bond between a "coordination site" of a first metal atom, $M^1$, and any one of the following: first ligand; bridging moiety; first anionic hydrocarbyl radical; first labile ligand; or metal atom $M^2$. A "coordination bond" can also be a bond between a "coordination site" of a second metal atom, $M^2$, and any one of the following: second ligand; bridging moiety; second anionic hydrocarbyl radical; second labile ligand; or metal atom $M^1$. A set of coordination bonds is represented by the symbol "A", having a superscript denoting the position of that bond in the "neutral metal-pair complex formula" (vide infra) and a subscript denoting the number of coordination bonds.

The term "ligand" has its usual meaning in organometallic chemistry. A "ligand" is a moiety bearing one or more "donor sites", wherein a "donor site" is an electron rich site (e.g., lone electron pair) capable of forming a "coordination bond" with a metal atom by donating electron density to an unoccupied (i.e., electron deficient) "coordination site" on that metal atom. The donor site is said to be "occupying that coordination site" on that metal atom. Alternatively, the ligand is said to be "coordinately bound" to the metal atom. When one or more coordination bonds exist between a ligand and a metal atom, both that ligand and that metal atom are said to be "participating" in each of those coordination bonds.

A "neutral electron donor ligand" is any ligand which, when removed from a metal atom (i.e., one or more coordination bonds are broken) in its closed shell electron configuration, has a neutral charge. For example, triphenylphosphine is a neutral electron donor ligand.

A "monodentate ligand" is a ligand bearing a single "donor site". For example, triphenylphosphine is a monodentate ligand, the phosphorus lone electron pair of which is a donor site capable of coordinating to (i.e., occupying a coordination site of) a metal atom.

A "bidentate ligand" is a ligand bearing two donor sites. For example, 1,2-bis(diphenylphosphino)ethane is a bidentate ligand. Each of the two donor sites of a bidentate ligand may be able to form a coordination bond to the same metal atom. Alternatively, one donor site of a bidentate ligand may form a coordination bond to one metal atom, while the other donor site of the same bidentate ligand may form a coordination bond to a different metal atom.

A "multi-dentate ligand" bears two or more donor sites, each of which is capable of coordinating to a metal atom. For example, pentamethyldiethylenetriamine is a multi-dentate ligand having three such donor sites. Provided that such considerations as steric and electronic factors allow it, each of the donor sites of a multi-dentate ligand may be able to form a coordination bond to the same metal atom. Alternatively, at least one donor site of a multi-dentate ligand may form a coordination bond to one metal atom, while at least one other donor site of the same multi-dentate ligand may form a coordination bond to a different metal atom, and each of those two metal atoms could be in the same metal-atom pair, or in two different metal-atom pairs of complex that contains one or more metal-atom pairs. A "bidentate ligand" is a special case of a "multi-dentate ligand".

It is further possible that fewer than all of the donor sites of a ligand may actually participate in coordination bonds. Therefore, for any ligand, the "effective number of donor sites" of that ligand is equal to the number of donor sites actually participating in coordination bonds. It follows that an "effectively monodentate ligand" is a ligand having a total of one donor site participating in a coordination bond. Similarly, for example, "effectively bidentate", "effectively tridentate", "effectively tetradentate", "effectively pentadentate", and "effectively hexadentate" ligands have, respectively, two, three, four, five, and six donor sites participating in coordination bonds. As a further example, pentamethyldiethylenetriamine has three amine lone electron pairs as donor sites, and is therefore a tridentate ligand. If only two of the amine lone electron pairs of this triamine were participating in coordination bonds with one metal, or two metals of a metal atom pair, the triamine would be effectively bidentate with respect to that metal atom pair. If only one of those electron pairs were participating in a coordination bond with a metal, the triamine would be effectively monodentate. As a further example, the allyl anion is effectively monodentate in its $\eta^1$-allyl form, but effectively bidentate in its $\eta^3$-allyl form.

A "first ligand" may be any ligand capable of participating in one or more coordination bonds with metal atom $M^1$ of a metal atom pair, while not simultaneously participating in a coordination bond with metal atom $M^2$ of that same metal atom pair.

A "second ligand" may be any ligand capable of participating in one or more coordination bonds with metal atom $M^2$ of a metal atom pair, while not simultaneously participating in a coordination bond with metal atom $M^1$ of that same metal atom pair.

A "third ligand" of the present invention may be any ligand capable of participating, simultaneously, in at least one coordination bond with each of metal atom $M^1$ and metal atom $M^2$, of the same metal atom pair.

A "labile neutral electron donor ligand" is any neutral electron donor ligand which is not strongly bound to a metal atom (e.g., $M^1$ or $M^2$), and is easily displaced therefrom. The terms "labile neutral electron donor ligand" and "labile ligand" are used interchangeably herein.

A "first labile ligand" is a labile ligand capable of participating in a coordination bond with metal atom $M^1$, while not simultaneously participating in a coordination bond with metal atom $M^2$.

A "second labile ligand" is a labile ligand capable of participating in a coordination bond with metal atom $M^2$, while not simultaneously participating in a coordination bond with metal atom $M^1$.

An anionic ligand, is any ligand which, when removed from a metal atom (e.g., $M^1$ or $M^2$) in its closed shell electron configuration, has a negative charge.

A "multi-(metal pair) coupling moiety", referred to herein, interchangeably, as a "pair-coupling moiety" is any multi-dentate moiety capable of participating, simultaneously, in at least one coordination bond with each of at least two metal atom pairs of a single complex. A "pair-coupling moiety" includes multiple donor sites having constraints (for example, steric constraints, electronic constraints, or both) allowing one or more of those donor sites to participate in coordination bonds with one metal pair while, simultaneously, one or more of its other donor sites is participating in coordination bonds with another metal pair. Though not wishing to be bound by any particular theory, it is believed that the number of metal pairs that can simultaneously participate in one or more coordination bonds with the same pair-coupling moiety is governed by such considerations as, for example: steric constraints of the pair-coupling moiety; electronic constraints of the donor sites of the pair-coupling moiety; electronic and spatial characteristics of metal atoms $M^1$ and $M^2$ within and, where there are multiple metal-atom pairs in the same complex, between metal atom pairs; steric and electronic characteristics of any other first ligand, second ligand, bridging moiety, first anionic hydrocarbyl containing radical, second anionic hydrocarbyl containing radical, first labile ligand, or second labile ligand, that is simultaneously participating in a coordination bond, or bonds, with either metal atom $M^1$ or $M^2$ of each metal atom pair; the mole ratios of the pair-coupling moiety to the metal pairs; and the accessibility of donor sites (e.g., a pair-coupling moiety may be a porous polymeric structure, wherein some donor sites may be inaccessible to metal atom pairs). Further, the maximum number of metal atom pairs that may possibly be coordinately bound to a single pair-coupling moiety is equal to the number of donor sites on that pair-coupling moiety. However, one or more of the constraints listed supra may intervene to limit the number of metal atom pairs that are actually bound to a single pair-coupling moiety to a number less than that maximum value. It may also be the case that a single pair-coupling moiety may participate in multiple coordination bonds with one or both of metal atoms $M^1$ and $M^2$ of a single metal pair. There is no particular limit on the size of the pair-coupling moiety. For example, the pair-coupling moiety may be a macroreticular resin bearing donor sites (vide infra), a crown ether, or other macro-structure bearing multiple donor sites. A "pair-coupling moiety" may be any of the following: first ligand, second ligand, third ligand, first labile ligand, second labile ligand, first hydrocarbyl radical, second hydrocarbyl radical, or combinations thereof. When two or more metal atom pairs are present in a neutral metal-pair complex of the present invention: all of metal atoms $M^1$ may be identical (e.g., all might be Ni); all of metal atoms $M^2$ may be identical; metal atom $M^1$ may differ from pair to pair (e.g., one might be Ni, while another would be Pd); and metal atom $M^2$ may differ from pair to pair.

A "neutral metal-pair complex" is a complex represented by the following "neutral metal-pair complex formula" ("formula I"):

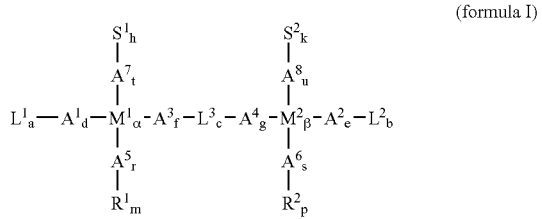
(formula I)

and the following symbols and subscripts have these meanings in the neutral metal-pair complex formula:

The symbols "$M^1$" and "$M^2$" represent, respectively, a first metal atom of a metal atom pair and a second metal atom of a metal atom pair.

The symbol "$L^1$" represents a "set of first ligands", wherein a "first ligand" is a ligand coordinately bound to metal atom $M^1$, but not coordinately bound to metal atom $M^2$. This set of first ligands may, interchangeably, be referred to as "set $L^1$". The neutral metal-pair complex formula subscript "a", of "$L^1_a$", equals either the integer 0 or 1. When "a"=1, set $L^1$ includes one or more first ligands. When "a"=0, set $L^1$ is "empty". When a ligand set is empty, that ligand set contains no ligands. For example, when "a"=0, set $L^1$ contains no first ligands.

The symbol "$L^2$", represents a "set of second ligands", wherein a "second ligand" is a ligand coordinately bound to metal atom $M^2$, but not coordinately bound to metal atom $M^1$. This set of second ligands may, interchangeably, be referred to as "set $L^2$". The neutral metal-pair complex formula subscript "b", of "$L^2_b$", equals either 0 or 1. When "b"=1, set $L^2$ includes one or more second ligands. When "b"=0, set $L^2$ is empty.

The symbol "$L^3$" represents a "set of bridging moieties". A "bridging moiety" is a moiety coordinately bound to both metal atom $M^1$ and metal atom $M^2$ of the same metal atom pair. A metal-metal bond is a special case of a bridging moiety wherein the moiety is the bond itself, and involves no other atoms beyond the two metal atoms of the metal-metal bond. A set of bridging moieties may, interchangeably, be referred to as "set $L^3$". The neutral metal-pair complex formula subscript "c", of "$L^3_c$", equals 1 in the neutral metal-pair complex formula, indicating that set $L^3$ includes one or more bridging moieties.

The symbol "$R^1$" represents a "set of first anionic hydrocarbyl containing radicals" coordinately bound to metal atom $M^1$, but not to metal atom $M^2$. This set of first anionic hydrocarbyl containing radicals may, interchangeably, be referred to as "set $R^1$". Herein, the term "first hydrocarbyl radical" is used interchangeably with the term "first anionic hydrocarbyl containing radical". The neutral metal-pair complex formula subscript "m", of "$R^1_m$", equals either 0 or 1. When "m"=1, set $R^1$ includes one or more first hydrocarbyl radicals. When "m"=0, set $R^1$ is empty.

The symbol "$R^2$" represents a "set of second anionic hydrocarbyl containing radicals" coordinately bound to metal atom $M^2$, but not to metal atom $M^1$. This set of second anionic hydrocarbyl containing radicals may, interchangeably, be referred to as "set $R^2$". Herein, the term "second hydrocarbyl radical" is used interchangeably with the term "second anionic hydrocarbyl containing radical". The subscript "p", of "$R^2_p$", equals either the integer 0 or 1. When subscript "p"=1, set $R^2$ includes one or more second hydrocarbyl radicals. When subscript "p"=0, set $R^2$ is empty. The relationship that, if one of the sets $R^1$ and $R^2$ is empty, then the other set must contain at least one anionic hydrocarbyl containing radical is represented by the following relationship: $1 \leq m+p \leq 2$.

It is also possible for a hydrocarbyl radical to simultaneously participate in at least one coordination bond of each of first metal atom, $M^1$, and second metal atom, $M^2$, of the same metal atom pair. This case is described herein as a "third anionic hydrocarbyl containing radical", alternatively "third hydrocarbyl radical". A "third hydrocarbyl radical" is a special case of a "bridging moiety", $L^3$.

An "anionic hydrocarbyl containing radical" (interchangeably, "hydrocarbyl radical") is any hydrocarbyl radical which, when removed from a metal atom (e.g., $M^1$ or $M^2$) in its closed shell electron configuration, has a negative charge. In any complex of the present invention in which they both are present, a first hydrocarbyl radical and a second hydrocarbyl radical may be the same or different. When a set $R^1$ contains more than one first hydrocarbyl radical, those first hydrocarbyl radicals may all be the same, or one or more may be different from at least one other first hydrocarbyl radical of that set $R^1$. When a set $R^2$ contains more than one second hydrocarbyl radical, those second hydrocarbyl radicals may all be the same, or one or more may be different from at least one other second hydrocarbyl radical of that set $R^2$.

The symbol "$S^1$" represents a "set of first labile ligands", wherein a "first labile ligand" is a labile ligand coordinately bound to metal atom $M^1$, but not coordinately bound to metal atom $M^2$. This set of first labile ligands may, interchangeably, be referred to as "set $S^1$". The neutral metal-pair complex formula subscript "h", of "$S^1_h$", equals either 0 or 1. When "h"=1, set $S^1$ includes one or more first labile ligands. When "h"=0, set $S^1$ is "empty". When a labile ligand set is empty, that labile ligand set contains no ligands. For example, when "h"=0, set $S^1$ is empty. When set $S^1$ contains more than one first labile ligand, those first labile ligands may all be the same, or one or more may be different from at least one other first labile ligand of that set $S^1$.

The symbol "$S^2$" represents a "set of second labile ligands", wherein a "second labile ligand" is a labile ligand coordinately bound to metal atom M 2, but not coordinately bound to metal atom $M^1$. This set of second labile ligands may, interchangeably, be referred to as "set $S^2$". The neutral metal-pair complex formula subscript "k", of "$S^2_k$", equals either 0 or 1. When "K"=1, set $S^2$ includes one or more second labile ligands. When "k"=0, set $S^2$ is empty. When a set $S^2$ contains more than one second labile ligand, those second labile ligands may be all the same, or one or more may be different from at least one other second labile ligand of that set $S^2$. In any neutral metal-pair complex of the present invention in which they both are present, a first labile ligand and a second labile ligand may be the same or different.

It is also possible for a labile ligand to simultaneously participate in at least one coordination bond of each of first metal atom, $M^1$, and second metal atom, $M^2$, of the same metal atom pair. This case is described herein as a "third labile ligand". A "third labile ligand" is a special case of a "bridging moiety", $L^3$.

The symbol "$A^1$" represents a set of coordination bonds between any first ligands of set $L^1$ and first metal atom, $M^1$ of a metal atom pair of the neutral metal-pair complex.

The symbol "$A^2$" represents a set of coordination bonds between any second ligands of set $L^2$ and second metal atom, $M^2$ of a metal atom pair of the neutral metal-pair complex.

The symbol "$A^3$" represents a set of coordination bonds between any bridging moieties of set $L^3$ and first metal atom, $M^1$ of a metal atom pair of the neutral metal-pair complex.

The symbol "$A^4$" represents a set of coordination bonds between any bridging moieties of set L and second metal atom, $M^2$ of a metal atom pair of the neutral metal-pair complex.

The symbol "$A^5$" represents a set of coordination bonds between any first hydrocarbyl radicals of set $R^1$ and first metal atom, $M^1$ of a metal atom pair of the neutral metal-pair complex.

The symbol "$A^6$" represents a set of coordination bonds between any second hydrocarbyl radicals of set $R^2$ and second metal atom, $M^2$ of a metal atom pair of the neutral metal-pair complex.

The symbol "$A^7$" represents a set of coordination bonds between any first labile ligands of set $S^1$ and first metal atom, $M^1$ of a metal atom pair of the neutral metal-pair complex.

The symbol "$A^8$" represents a set of coordination bonds between any second labile ligands of set $S^2$ and second metal atom $M^2$ of a metal atom pair of the neutral metal-pair complex.

Any of the sets of coordination bonds represented by the symbol "A" may, interchangeably, be referred to as "set A". For example, the set of coordination bonds represented by the symbol "$A^1$" may, interchangeably, be referred to as "set $A^1$".

If any of sets $L^1$, $L^2$, $R^1$, $R^2$, $S^1$, and $S^2$ is empty, the neutral metal-pair complex formula subscript of any symbol "A" representing any coordination bonds directly associated with that set will equal 0. For example, if set $L^1$ is empty, "a" of "$L^1_a$" equals 0, and "d" of "$A^1_d$", also equals 0. It follows that, if any of neutral metal-pair complex formula subscripts "a", "b", "h", "k", "m", and "p" equal 0, then the corresponding neutral metal-pair complex formula subscripts "d", "e", "t", "u", and "s" will, respectively, equal 0.

If any of sets $L^1$, $L^2$, $L^3$, $R^1$, $R^2$, $S^1$, and $S^2$ is occupied, i.e., contains at least one member of its set, the neutral metal-pair complex formula subscript of any symbol "A", representing any coordination bonds directly associated with a member of that set, will equal at least 1. That is, for any of sets $L^1$, $L^2$, $L^3$, $R^1$, $R^2$, $S^1$, and $S^2$ that are occupied, the corresponding neutral metal-pair complex formula subscripts d, e, f, g, r, s, t, or u will, respectively, equal at least 1. For example, if set $L^1$ of a "neutral metal-pair complex" is occupied, "a" of "$L^1_a$" equals 1, and "d" of "$A^1_d$" equals at least 1. Further, if any of sets $L^1$, $L^2$, $L^3$, $R^1$, $R^2$, $S_1$, and $S^2$ is occupied, and the neutral metal-pair complex formula subscript of a symbol "A" representing coordination bonds directly associated with a member, or members, of that set equals at least 2, the plural coordination bonds indicated by that subscript may all emanate from a single member of that set, or, alternatively, emanate from more than one member of that set. For example, if "e", of "$A^2_e$", equals the integer 3, then set $L^2$ may contain one, two, or three second ligands. In this example, set $L^2$ may contain any of these combinations: three effectively monodentate second ligands (vide supra); one effectively monodentate second ligand and one effectively bidentate second ligand; or one effectively tridentate second ligand.

When a "metal-metal bond" exists between first metal atom, $M^1$, and second metal atom, $M^2$, of a metal atom pair of a neutral metal-pair complex, the presence of that metal-metal bond is indicated in the neutral metal-pair complex formula by incrementing both of subscripts "f" and "g" by 1. In this specific case of a metal-metal bond, the combination of an $A^3$ bond and an $A^4$ bond represents one single bond because there exist no atoms in the bridging moiety, that is, the electron cloud of the bond between metal atom $M^1$ and metal atom $M^2$ is the bridging moiety.

A "bridging moiety" of set $L^3$ may be a third ligand, bridging labile ligand, bridging anionic hydrocarbyl radical, bridging hemi-labile ligand, or metal-metal bond.

The "neutral metal-pair complex formula subscripts" have values which are either positive integers or zero. Neutral metal-pair complex formula subscripts have these definitions: a, b, h, k, m, and p are independently selected from 0 or 1; c equals 1; $1 \leq m+p \leq 2$; the sum d+f+r+t=4, 5, or 6; and sum e+g+s+u=4, 5, or 6; with the proviso that i) when the sum d+f+r+t=4, $M^1$ is selected from nickel, palladium, copper, iron, cobalt, rhodium, chromium, and manganese; d, r, and t are selected from 0, 1, 2, and 3; and f is selected from 1, 2, 3, and 4; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 5$; $1 \leq r+s \leq 5$; $0 \leq t+u \leq 5$; and $2 \leq f+g \leq 7$;

when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 6$; $1 \leq r+s \leq 6$; $0 \leq t+u \leq 6$; and $2 \leq f+g \leq 8$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 7$; $1 \leq r+s \leq 7$; $0 \leq t+u \leq 7$; and $2 \leq f+g \leq 9$;

(ii) when the sum d+f+r+t=5;

$M^1$ is selected from iron, cobalt, ruthenium, rhodium, chromium, and manganese; d, r, and t are selected from 0, 1, 2, 3, and 4; f is selected from 1, 2, 3, 4, and 5; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 6$; $1 \leq r+s \leq 6$; $0 \leq t+u \leq 6$; and $2 \leq f+g \leq 8$;

when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 7$; $1 \leq r+s \leq 7$; $0 \leq t+u \leq 7$; and $2 \leq f+g \leq 9$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 8$; $1 \leq r+s \leq 8$; $0 \leq t+u \leq 8$; and $2 \leq f+g \leq 10$; and (iii) when the sum d+f+r+t=6;

$M^1$ is selected from copper, iron, cobalt, ruthenium, rhodium, chromium, and manganese; d, r, and t are selected from 0, 1, 2, 3, 4, and 5; f is selected from 1, 2, 3, 4, 5, and 6; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 7$; $1 \leq r+s \leq 7$; $0 \leq t+u \leq 7$; and $2 \leq f+g \leq 9$;

when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 8$; $1 \leq r+s \leq 8$; $0 \leq t+u \leq 8$; and $2 \leq f+g \leq 10$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 9$; $1 \leq r+s \leq 9$; $0 \leq t+u \leq 9$; and $2 \leq f+g \leq 11$.

The "first precursor complex" of the present invention is a complex according to the first precursor complex formula II

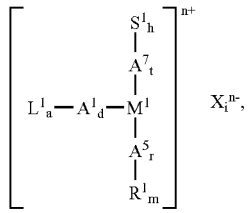  (II)

wherein:
$L^1$ is a set of first ligands;
$R^1$ is a set of first anionic hydrocarbyl containing radicals;
$S^1$ is a set of first labile ligands;
X is a set of anionic counter ions;
$A^1, A^5, A^7$ are sets of coordination bonds;
a, h, m, and i are independently selected from 0 and 1;
n=0, 1, 2, or 3; when n=0, i=0; when n=1, 2, or 3, i=1; and
the sum d+r+t=4, 5, or 6;
with the proviso that
(i) when the sum d+r+t=4,
 $M^1$ is selected from nickel, palladium, copper, iron, cobalt, rhodium, chromium, and manganese;
 d is selected from 0, 1, 2, 3, and 4; and
 r and t are selected from 0, 1, 2, and 3;
(ii) when the sum d+r+t=5,
 $M^1$ is selected from iron, cobalt, ruthenium, rhodium, chromium, and manganese;
 d is selected from 0, 1, 2, 3, 4, and 5; and
 r and t are selected from 0, 1, 2, 3, and 4; or
(iii) when the sum d+r+t=6
 $M^1$ is selected from copper, iron, cobalt, ruthenium, rhodium, chromium, and manganese;
 d is selected from 0, 1, 2, 3, 4, 5, and 6; and
 r and t are selected from 0, 1, 2, 3, 4, and 5.

The "second precursor complex" of the present invention is a complex according to the second precursor complex formula III

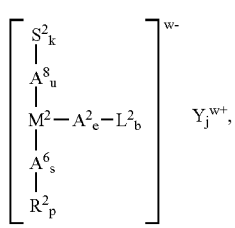  (III)

wherein:
$L^2$ is a set of second ligands;
$R^2$ is a set of second anionic hydrocarbyl containing radicals;
$S^2$ is a set of second labile ligands;
Y is a set of cationic counter ions;
$A^2, A^6, A^8$ sets of coordination bonds;
b, k, p, and j are independently selected from 0 and 1;
n=0, 1, 2, or and
the sum e+s+u=4, 5, or 6;
with the proviso that
(i) when the sum e+s+u=4,
 $M^2$ is selected from nickel, palladium, copper, iron, cobalt, rhodium, chromium, and manganese;
 e is selected from 0, 1, 2, 3, and 4; and
 s and u are selected from 0, 1, 2, and 3;
(ii) when the sum e+s+u=5,
 $M^2$ is selected from iron, cobalt, ruthenium, rhodium, chromium, and manganese;
 e is selected from 0, 1, 2, 3, 4, and 5; and
 s and u are selected from 0, 1, 2, 3, and 4; or
(iii) when the sum e+s+u=6
 $M^2$ is selected from copper, iron, cobalt, ruthenium, rhodium, chromium, and manganese;
 e is selected from 0, 1, 2, 3, 4, 5, and 6; and
 s and u are selected from 0, 1, 2, 3, 4, and 5.

For any reaction between a first precursor complex and a second precursor complex, at least one of subscripts m and p must equal 1 (i.e., $1 \leq m+p \leq 2$), indicating that at least one anionic hydrocarbyl radical must be present.

The symbol "X" represents a "set of anionic counter ions", wherein an "anionic counter ion" is an anion which is weakly associated with metal atom $M^1$, but not coordinately bound to metal atom $M^1$. This set of anionic counter ions may, interchangeably, be referred to as "set X". The subscript "i", of "$X_i$", equals either 0 or 1. When "i"=1, set X includes one or more anionic counter ions. When "i"=0, set X is empty.

The symbol "Y" represents a "set of cationic counter ions", wherein a "cationic counter ion" is a cation which is weakly associated with metal atom $M^2$, but not coordinately bound to metal atom $M^2$. This set of cationic counter ions may, interchangeably, be referred to as "set Y". The subscript "j", of "$Y_j$", equals either 0 or 1. When "j"=1, set Y includes one or more cationic counter ions. When "j"=0, set Y is empty.

Further, superscripts n and w, respectively, of $X_i^{n-}$ and $Y_j^{w+}$ must be equal, so that, upon reaction to form a neutral metal-pair complex, the charge of that neutral metal-pair complex will be zero. Subscript j must equal subscript i. For example, when both the first and second precursor complexes are neutral (w=n=0), there will be no anionic or cationic counter ion, hence both counter ion sets X and Y will be empty 0=i=0), and when both first and second precursor complexes are charged (w=n=1, 2, or 3), there will be at least one anionic counter ion in set X and at least one cationic counter ion in set Y, hence j=i=1.

Symbols "$M^1$", "$R^1$", "$L^1$", and "$S^1$" of the "first precursor complex formula" have, respectively, the same meaning as the symbols "$M^1$", "$R^1$", "$L^1$", and "S" of the "neutral metal-pair complex formula".

Symbols "$M^2$", "$R^2$", "$L^2$", and "$S^2$" of the "second precursor complex formula" have, respectively, the same meaning as the symbols "$M^2$", "$R^2$", "$L^2$", and "$S^2$" of the "neutral metal-pair complex formula".

Symbols "$A^1$", "$A^5$", and "$A^7$" of the "first precursor complex formula" have, respectively, the same meaning as the symbols "$A^1$", "$A^5$", and "$A^7$" of the "neutral metal-pair complex formula".

Symbols "A²", "A⁶", and "A⁸" of the "second precursor complex formula" have, respectively, the same meaning as the symbols "A²", "A⁶", and "A⁸" of the "neutral metal-pair complex formula".

The term "ethylenically unsaturated monomer" refers to a molecule having one or more carbon-carbon double bonds, and capable of insertion addition polymerization. The term "monoethylenically unsaturated monomer" refers to an ethylenically unsaturated monomer having one carbon-carbon double bond capable of insertion addition polymerization. The term "multiethylenically unsaturated monomer" refers to an ethylenically unsaturated monomer having two or more carbon-carbon double bonds capable of insertion addition polymerization.

The term "non-polar olefinic monomer" (alternatively "non-polar olefin") refers to an ethylenically unsaturated monomer consisting exclusively of hydrogen and carbon atoms. The non-polar olefinic monomers of the present invention are any non-polar olefinic monomers capable of being polymerized using the neutral metal-pair complex of the present invention to form "poly(non-polar olefin)s" or "poly [(polar olefin)-(non-polar olefin)]s".

The term "polar olefinic monomer" (alternatively "polar olefin") refers to an ethylenically unsaturated monomer including at least one atom other than carbon or hydrogen. The polar olefinic monomers of the present invention are any non-polar olefinic monomers capable of being polymerized using the neutral metal-pair complex of the present invention to form "poly(polar olefin)s" or "poly[(polar olefin)-(non-polar olefin)]s".

The term "(meth)acryl" refers to both "acryl" and "methacryl". For example, "butyl (meth)acrylate" refers to both "butyl acrylate" and "butyl methacrylate". "(Meth)acryl" type monomers are examples of the "polar olefinic monomer" of the present invention.

An "addition polymer" is a polymer capable of being prepared by addition polymerization, and selected from the group consisting of poly(non-polar olefin), poly(polar olefin), poly[(polar olefin)-(non-polar olefin)], and combinations thereof.

A "poly(non-polar olefin)" is a polymer comprising one or more non-polar olefinic monomers, as polymerized units. As such, a "poly(non-polar olefin)" may be a homopolymer or a copolymer, and the copolymer may be, for example, a random, alternating, or block copolymer.

A "poly(polar olefin)" is a polymer comprising, as polymerized units, one or more polar olefinic monomers. As such, a "poly(polar olefin)" may be a homopolymer or a copolymer, and the copolymer may be, for example, a random, alternating, or block copolymer.

A "poly[(polar olefin)-(non-polar olefin)]" is a copolymer comprising one or more non-polar olefinic monomers and one or more polar olefinic monomers, as polymerized units, and the copolymer may be, for example, a random, alternating, or block copolymer. The addition polymer of the present invention is a polymer selected from the group consisting of: poly(non-polar olefin), poly(polar olefin), poly[(polar olefin)-(non-polar olefin)], and combinations thereof.

The following expressions describe the molecular weight of a collection of polymer chains "weight average molecular weight", "$M_w$" and the "number average molecular weight", "$M_n$". These are defined as follows:

$$M_w = \Sigma(W_i M_i)/\Sigma W_i = \Sigma(N_i M_i^2)/\Sigma N_i M_i$$

$$M_n = \Sigma W_i / \Sigma(W_i/M_i) = \Sigma(N_i M_i)/\Sigma N_i$$

where:
$M_i$=molar mass of $i^{th}$ component of distribution
$W_i$=weight of $i^{th}$ component of distribution
$N_i$=number of chains of $i^{th}$ component and the summations are over all the components in the distribution. $M_w$ and $M_n$ are typically computed from the MWD as measured by Gel Permeation Chromatography (see the Experimental Section). The value for "$M_w/M_n$" is referred to as the "MWD polydispersity".

The "average particle size" determined for a collection of polymer particles, varies somewhat according to method of determination (e.g., by DCP or BI-90, as described herein below), but is approximately, or identically, "the weight average particle size", "$d_w$", also described herein below.

Herein, the term "particle size distribution" and the acronym "PSD" are used interchangeably. Used herein, "PSD polydispersity" is a description of the distribution of particle sizes for the plural polymer particles of the invention. PSD polydispersity is calculated from the weight average particle size, $d_w$, and the number average particle size, $d_n$, according to the expressions:

$$PSD \text{ Polydispersity}=(d_w)/(d_n)$$

where $$d_n = \Sigma n_i d_i / \Sigma n_i$$

$$d_w = \Sigma n_i d_i^2 / \Sigma n_i d_i, \text{ and}$$

where $n_i$ is the number of particles having the particle size $d_i$

A "monodisperse" distribution (herein, MWD or PSD) refers to a distribution having a polydispersity of exactly 1.

A "supercritical fluid" ("SCF") is a substance above its critical temperature and critical pressure (i.e., its "critical point"). For carbon dioxide, the critical temperature is 31° C. and the critical pressure is 1070 psi. Above the critical point of a fluid, further compression does not cause formation of a liquid (see *Chem. Rev.*, 1999, 99, pp. 565-602).

Each metal atom pair of the neutral metal-pair complex of the present invention includes a single "first metal atom" represented by the symbol "$M^1$" ("metal atom $M^1$") and a single "second metal atom" represented by the symbol "$M^2$" ("metal atom $M^2$"). The first and second metal atoms of the neutral metal-pair complex can, independently, have: four (4) occupied coordination sites; five (5) occupied coordination sites; or six (6) occupied coordination sites. When a first or second metal atom of the neutral metal-pair complex has four (4) occupied coordination sites, that metal atom is a metal atom selected from: nickel, palladium, copper, iron, cobalt, rhodium, chromium, and manganese; nickel, palladium, copper, iron, and cobalt; or nickel and palladium. When a first or second metal atom of the neutral metal-pair complex has five (5) occupied coordination sites, that metal atom is a metal atom selected from: iron, cobalt, ruthenium, rhodium, chromium, and manganese; or iron, cobalt, and chromium. When a first or second metal atom of the neutral metal-pair complex has six (6) occupied coordination sites, that metal atom is a metal atom selected from: copper, iron, cobalt, ruthenium, rhodium, chromium, and manganese; or copper, iron, cobalt, and chromium.

Because the neutral metal-pair complex of the present invention is made from the first and second precursor complexes of the present invention, it follows that $M^1$ of a neutral metal-pair complex will be identical to $M^1$ of the first precursor complex from which it was made, and that that $M^2$ of a neutral metal-pair complex will be identical to $M^2$ of the second precursor complex from which it was made.

The combined molar percentage of first metal atom, $M^1$, and second metal atom, $M^2$, present in the neutral metal-pair complex of the present invention, based on the total of all $M^1$-type metal atoms and $M^2$-type metal atoms present in any catalyst complexes of the catalytic composition of the present invention, is: at least 25, at least 50, at least 75, at least 90, or at least 95; and no more than 100; no more than 99; or no more than 97, based on the total moles of $M^1$ and $M^2$ The "through-space internuclear distance" for a metal atom pair of the present invention is: at least 1.5 Angstroms (Å=0.0001 micron), at least 2 Å, at least 3 Å, or at least 4 Å; and no more than 20 Å, no more than 15 Å, no more than 10 Å, or no more than 6 Å.

Any monodentate or multidentate ligand may be a first ligand of set $L^1$ or a second ligand of set $L^2$ of the present invention, provided that constraints (e.g., electronic, steric, and other spatial constraints) which exist for the ligand in any given neutral metal-pair complex, or precursor complex allow that monodentate or multidentate ligand to participate in at least one coordination bond with the corresponding metal atom ($M^1$ for ligand set $L^1$; and $M^2$ for ligand set $L^2$) of a metal-atom pair.

When set $L^1$ and set $L^2$ are occupied, the first and second ligands that are, respectively, members of those sets may be identical or different ligands within a given set (i.e., $L^1$, $L^2$), and the ligands of set $L^1$ may be the same or different from those of set $L^2$. First ligands and second ligands may be, independently, selected from the following non-exhaustive lists of ligand types wherein at least one atom selected from Group 14, 15, 16, and 17 participates in at least one coordination bond of the present invention.

Any multidentate ligand may also be a third ligand of set $L^3$ of the present invention, provided that constraints (e.g., electronic, steric, and other spatial constraints) which obtain for the ligand in any specific neutral metal-pair complex allow that multidentate ligand to simultaneously participate in at least one coordination bond with each of the metals of a metal-atom pair of that neutral metal-pair complex. A proviso is that the third ligand cannot be 3,3'-bisalicylaldimine.

Similarly, lists of labile ligand, hemi-labile ligand, anionic hydrocarbyl containing radical, anionic counter ion, cationic counter ion, scavenger, diluent, and monomer types, as well as specific examples, provided herein are meant to be illustrative and not exhaustive. Further, the ability of a given labile ligand, hemi-labile ligand, or anionic hydrocarbyl containing radical to form a coordination bond with one, or both, metal atoms of a metal atoms pair of a particular neutral metal-pair complex or precursor complex of the present invention, will depend upon the constraints (e.g., electronic, steric, and other spatial constraints) which exist for that labile ligand, hemi-labile ligand, or anionic hydrocarbyl containing radical.

When mono- and multi-dentate ligands are indicated structurally or by chemical name herein, usage may be made of the designation of one or more substituents on a ligand as an "R-group" indicated by a capital "R", with or without a superscript. Although such notation, common in the art of organometallic chemistry and chemistry in general, is retained herein for describing substituents of ligands, it is understood, herein, that these "R-group" notations do not refer to set $R^1$ or set $R^2$ of the neutral metal-pair complex, or of the precursor complex, of the present invention. Similarly, it is understood that any R-group notations used herein to describe, for example, substituents of labile ligands, or substituents of hemi-labile ligands, or substituents of ethylenically unsaturated monomers, do not refer to set $R^1$ or set $R^2$ of the present invention.

Representative neutral electron donor ligands include amines, pyridines, organophosphorus containing compounds, and arsines and stibines, of the formula: $E(R^3)_3$, wherein E is arsenic or antimony, and $R^3$ is independently selected from hydrogen, linear and branched $C_1$-$C_{10}$ alkyl, $C_5$-$C_{10}$ cycloalkyl, linear and branched $C_1$-$C_{10}$ alkoxy, allyl, linear and branched $C_2$-$C_{10}$ alkenyl, $C_6$-$C_{12}$ aryl, $C_6$-$C_{12}$ aryloxy, $C_6$-$C_{12}$ arylsufides (e.g., PhS), $C_7$-$C_{18}$ aralkyl, cyclic ethers and thioethers, tri(linear and branched $C_1$-$C_{10}$ alkyl) silyl, tri($C_6$-$C_2$ aryl)silyl, tri(linear and branched $C_1$-$C_{10}$ alkoxy)silyl, triaryloxysilyl, tri(linear and branched $C_1$-$C_{10}$ alkyl)siloxy, and tri($C_6$-$C_{12}$ aryl)siloxy, each of the foregoing substituents can be optionally substituted with linear or branched $C_1$-$C_5$ alkyl, linear or branched $C_1$-$C_5$ haloalkyl, $C_1$-$C_5$ alkoxy, halogen, and combinations thereof.

Representative pyridines include pyridine, lutidine (including 2,3-; 2,4-; 2,5-; 2,6-; 3,4-; and 3,5-substituted), picoline (including 2-, 3-, or 4-substituted), 2,6-di-t-butylpyridine, and 2,4-di-t-butylpyridine.

Representative arsines include triphenylarsine, triethylarsine, and triethoxysilylarsine.

Representative stibines include triphenylstibine and trithiophenylstibine.

Suitable amine ligands can be selected from amines of the formula $N(R^4)_3$, wherein $R^4$ independently represents hydrogen, linear and branched $C_1$-$C_{20}$ alkyl, linear and branched $C_1$-$C_{20}$ haloalkyl, substituted and unsubstituted $C_3$-$C_{20}$ cycloalkyl, substituted and unsubstituted $C_6$-$C_{18}$ aryl, and substituted and unsubstituted $C_7$-$C_{18}$ aralkyl. When substituted, the cycloalkyl, aryl and aralkyl groups can be mono-substituted or multisubstituted, wherein the substituents are independently selected from hydrogen, linear and branched $C_1$-$C_{12}$ alkyl, linear and branched $C_1$-$C_5$ haloalkyl, linear and branched $C_1$-$C_5$ alkoxy, $C_6$-$C_{12}$ aryl, and halogen selected from chlorine, bromine, and fluorine.

The organophosphorus containing ligands include phosphines, phosphites, phosphonites, phosphinites and phosphorus containing compounds of the formula: $P(R^3)\,g\,[X'(R^3)_h]_{3-g}$, wherein X' is oxygen, nitrogen, or silicon, $R^3$ is as defined above and each $R^3$ substituent is independent of the other, g is 0, 1, 2, or 3, and h is 1, 2, or 3, with the proviso that when X' is a silicon atom, h is 3, when X' is an oxygen atom h is 1, and when X' is a nitrogen atom, h is 2. When g is 0 and X' is oxygen, any two or three of $R^3$ can be taken together with the oxygen atoms to which they are attached to form a cyclic moiety. When g is 3 any two of $R^3$ can be taken together with the phosphorus atom to which they are attached to represent a phosphacycle.

Illustrative phosphine ligands include, but are not limited to trimethylphosphine, triphenylphosphine, tri(trifluoromethylphenyl)phosphine, allyldiphenylphosphine, tris(trimethylsilyl)phosphine, and tris(pentafluorophenyl)phosphine.

Illustrative phosphite ligands include triethylphosphite, dicyclohexylphosphite, and tri(hexafluoroisopropyl)phosphite.

Illustrative phosphinite ligands include methyl diphenylphosphinite and ethyl diphenylphosphinite.

Illustrative phosphonite ligands include diphenyl phenylphosphonite and diethyl phenylphosphonite.

The multidentate ligands of the present invention include multidentate ligands containing identical or different donor atoms selected from Group 14, 15, 16, and 17 atoms. The substituents covalently bonded to those donor atoms selected from Group 14, 15, 16, and 17 atoms may be any of those bound to the Group 14, 15, 16, and 17 atoms of the monodentate ligands of the present invention.

Illustrative bidentate phosphine ligands of the present invention include (R)-(+)-2,2'-Bis(diphenylphosphino)-1,1'-binaphthy, and 1,2-bis(diphenylphosphino)ethane.

Additional neutral electron ligands useful in the present invention are disclosed in U.S. Pat. No. 6,455,650.

N-heterocyclic carbene ligands, suitable for use with the present invention include saturated and unsaturated substituted and unsubstituted imidazolidine carbenes including those disclosed in U.S. patent application no. US 2005/0043494 A1.

Additional moieties suitable as bridging moieties include methylenes, alkylenes, halides, and pseudohalides. The methylenes (i.e., $CR^3{}_2$) and alkylenes (i.e., $(CR^3{}_2)_n$, n=1-24), may have $R^3$-groups which, independently, may be C1-C20 alkyl or branched alkyl, mono and multi-ring aryl. Further, any of the carbons of these methylenes and alkylenes may be further substituted with functional groups. Halides and pseudohalides may be and first ligand, second ligands, or bridging moieties. Suitable halides include, for example, fluoride, chloride, bromide, and iodide. Suitable pseudohalides include, for example, cyanide, isocyanide, alkoxides, thioalkoxides, amines, and phosphides. Hydride may further be a bridging moiety. These and other suitable bridging moieties are disclosed in Gavrilova, A. L.; Bosnich, B. *Chem. Rev.* 2004, 104, 349, and in U.S. patent application no. US 2005/0043494 A1.

Hemilabile ligands contain at least two different types of donor sites, wherein at least one donor site is capable of acting as a "non-labile donor site", such as the donor sites of the first, second, and third ligands of the present invention, and at least one donor site is capable of acting as a "labile donor site", such as the donor sites of the first and second labile ligands of the present invention. Typically, a labile donor site is easily displaced from a coordination bond with a metal by, for example, the donor sites of labile ligands (e.g., solvent molecules) and by ethylenically unsaturated monomer. It, therefore, follows that a labile donor site of a hemi-labile ligand is easily displaced by strongly coordinating ligands, such as the first, second, and third ligands of the present invention. In contrast, a non-labile donor site is difficult to displace from coordination bond with a metal. Therefore, when a hemilabile ligand is attached to a metal pair of a neutral metal-pair complex or precursor complex of the present invention, the formalism for assigning subscripts to any neutral metal-pair complex formula or precursor complex formula is as follows: when a hemilabile ligand is bound to a single metal atom of a metal atom pair, any coordination bonds formed by any of the donor sites (labile or non-labile) of that hemilabile ligand will be treated as coordination bonds of first or second ligands; when a hemilabile ligand is bound to both metal atoms of a metal atom pair, any coordination bonds formed by any of the donor sites (labile or non-labile) of that hemilabile ligand will be treated as coordination bonds of a bridging moiety. Further description of hemilabile ligands may be found in: Braunstein, P.; Naud, F. *Angew. Chem. Int. Ed.* 2001, 40, 680; Slone, C. S.; Weinberger, D. A.; Mirkin, C. A. *Prog. Inorg. Chem.* 1999, 48, 233, and the hemilabile ligands of the present invention include those disclosed therein.

In one embodiment of the neutral metal-pair complex (formula I) of the present invention, when both the sum d+f+r+t=4 and the sum e+g+s+u=4, a bridging moiety includes no more than one atom selected from O and S bonded directly to a metal atom of the same metal atom pair. For example, if an oxygen atom or a sulfur atom of a bridging moiety forms a coordination bond with first metal atom, $M^1$, there will be no additional oxygen atom or sulfur atom of that same bridging moiety forming a coordination bond with second metal atom, $M^2$, of the same metal atom pair, unless that single oxygen atom or sulfur atom is simultaneously bonded to both M1 and M2.

In another embodiment of the neutral metal-pair complex (formula I) of the present invention, when both the sum d+f+r+t=4 and the sum e+g+s+u=4, the bridging moiety includes no atom selected from O and S bonded directly to either of first metal atom, $M^1$, and second metal atom, $M^2$, of the same metal atom pair.

One skilled in the art of organometallic chemistry will recognize that the hemilabile ligands of the present invention may be any hemilabile ligand. For illustrative purposes, a non-exhaustive list of hemi-labile phosphine ligands is described. Similar lists exist for other Group 14, 15, 16, and 17 atom containing ligands. By hemilabile phosphine ligand is meant a phosphine ligand containing an additional heteroatom substituent, (e.g., oxygen or sulfur), capable of weakly complexing a metal atom. Included in the hemilabile phosphine ligands of the present invention are hemilabile phosphine ligands represented by the formula $P(R^{24})_2Q$ wherein $R^{24}$ independently represents linear and branched ($C_1$-$C_{12}$) alkyl, cycloalkyl and ($C_6$-$C_{14}$) aryl and substituted aryl, and Q represents an organic moiety containing a heteroatom, selected from phosphorous, oxygen, and sulfur and combinations thereof. Examples of the Q substituent include but are not limited to -dibenzothiophene, ortho-alkoxyphenyl-, ortho-alkoxycarbonylphenyl-, wherein the alkoxy group is linear or branched ($C_1$-$C_5$) alkoxy; —$(CH_2)_qS(=O)C_6H_5$, —$(CH_2)_qSC_6H_5$, —$(CH_2)_qP(=O)(C_6H_5)_2$, —$(CH_2)_qP(=S)(C_6H_5)_2$, wherein q is 2 or 3. Examples of ligands excluded from this class of hemilabile ligands are the strongly chelating ligands, e.g., the diphosphines such as diphenylphosphinoethane and diphenylphosphinopropane.

A non-exhaustive list of the labile neutral electron donor ligands (i.e., labile ligands) of the present invention includes solvents such as methylene chloride, $CHCl_3$, $ClCH_2CH_2Cl$, acrylonitrile, tetrahydrofuran, toluene, benzene, chlorobenzene, and polar monomers, as well as any other diluents typified by those found in the list of diluents, herein, which are able to donate electron density to a metal atom coordination site to form a coordination bond. Further, molecules such as, for example, dioxane, crown ethers, other polyethers, and cyclodextrins typify labile ligands capable of bridging between the metal atoms of a metal atom pair, and, where electronic, steric, and special constraints permit, between, or among metal atom pairs. One skilled in the art of organometallic chemisty will understand that a labile ligand may participate in a coordination bond with a one or both metal atoms of a metal atom pair. Alternatively, a labile ligand may be more loosely associated as part of a solvation sphere which may, in some cases, surround any of the neutral metal-pair complexes or precursor complexes of the present invention. According to common practice in the art, these more loosely associated molecules of the solvation sphere are not explicitly indicated in the neutral metal-pair complex formula or the precursor complex formula.

An anionic hydrocarbyl containing radical may be a member of sets $R^1$ and $R^2$ of the neutral metal-pair complex, and, respectively, of the first or second precursor complexes of the present invention. $R^1$ and $R^2$ may be, independently, selected from the following non-exhaustive lists of types of anionic hydrocarbyl containing ligand and of specific examples of anionic hydrocarbyl containing ligand.

First and second anionic hydrocarbyl containing radicals include, but are not limited to, hydrogen, linear and branched C1-C20 alkyl, C5-C10 cycloalkyl, linear and branched C2-C20 alkenyl, C6-C15 cycloalkenyl, allylic and methallylic ligands, crotyl ligands, or canonical forms thereof, C6-C30 aryl, C6-C30 heteroatom containing aryl, and C7-C30 aralkyl, each of the foregoing groups can be optionally substituted with hydrocarbyl containing and/or heteroatom substituents preferably selected from linear or branched C1-C5 alkyl, linear or branched C1-C5 haloalkyl, linear or branched C2-C5 alkenyl and haloalkenyl, halogen, sulfur, oxygen, nitrogen, phosphorus, and phenyl optionally substituted with linear or branched C1-C5 alkyl, linear or branched C1-C5 haloalkyl, and halogen. $R^1$ and $R^2$ also represent anionic containing radicals of the formula R"C(O)O, R"C(O)CHC(O)R", R"C(O)S, R"C(S)O, R"C(S)S, R"O, and R"$_2$N. Additional examples of anionic hydrocarbyl containing radicals are disclosed in U.S. Pat. No. 6,455,650; U.S. patent application no. US 2005/0043494 A1; Guy, R. G.; Shaw, B. L. *Advances in Inorganic Chemistry and Radiochemistry*, Vol. 4, Academic Press Inc., New York, 1962; Birmingham, J. et al., *Advances in Organometallic Chemistry*, Vol. 2, Academic Press Inc., New York, 1964; Dent, W. T.; Long, R.; Wilkinson, A. J. *J. Chem. Soc.*, 1964 1585; and Volger, H. C. *Rec. Trav. Chim. Pay Bas*, 1969 88 225.

A non-exhaustive list of anionic counter ions includes $H^+$ and its complexes, naked alkali metal cations ($Li^+$, $Na^+$, $K^+$, $Rb^+$, $Cs^+$) and their complexes of the same charge, alkali earth metal cations ($Be^{2+}$, $Mg^{2+}$, $Ca^{2+}$, $Sr^{2+}$, $Ba^{2+}$) and their complexes of the same charge, naked transition metal cations ($M^+$, $M^{2+}$, $M^{3+}$) and their complexes of the same charge, naked f block metal cations ($M^+$, $M^{2+}$, $M^{3+}$) and their complexes of the same charge, Group XIII metal cations ($M^+$, $M^{2+}$, $M^{3+}$) and their complexes of the same charge, $C(R^1)(R^2)(R^3)^+$ (each of $R^1$, $R^2$, $R^3$, and $R^4$ is selected from C1~C30 alkyl groups or their substituted analogues, C1~C30 alkenyl groups or their substituted analogues, C1~C30 alkynyl groups or their substituted analogues, C6~C60 aryl groups or their substituted analogues), $Si(R^1)(R^2)(R^3)^+$ (each of $R^1$, $R^2$, $R^3$, and $R^4$ is selected from C1~C30 alkyl groups or their substituted analogues, C1~C30 alkenyl groups or their substituted analogues, C1~C30 alkynyl groups or their substituted analogues, C6~C60 aryl groups or their substituted analogues), $N(R^1)(R^2)(R^3)(R^4)^+$ (each of $R^1$, $R^2$, $R^3$, and $R^4$ is selected from C1~C30 alkyl groups or their substituted analogues, C1~C30 alkenyl groups or their substituted analogues, C1~C30 alkynyl groups or their substituted analogues, C6~C60 aryl groups or their substituted analogues), $P(R^1)(R^2)(R^3)(R^4)^+$ (each of $R^1$, $R^2$, $R^3$, and $R^4$ is selected from C1~C30 alkyl groups or their substituted analogues, C1~C30 alkenyl groups or their substituted analogues, C1~C30 alkynyl groups or their substituted analogues, and C6~C60 aryl groups or their substituted analogues).

A non-exhaustive list of cationic counter ions includes borates (e.g., bis(trifluoromethyl)phenyl)borate) and aluminates (e.g., tetrakis(pentafluorophenyl)aluminate), boratobenzene anions (e.g., [1,4-dihydro-4-methyl-1-(pentafluorophenyl)]-2-borate), carborane halocarborane anions, antimony halide anions (e.g., $SbF_6$), phosphorus halide anions (e.g., $PF_6$), and boron halide anions (e.g., $BF_4$). The cationic counter ions of the present invention further include any of the weakly coordinating anions disclosed in U.S. Pat. No. 6,455,650 and patent application no. US 2005/0043494 A1.

The non-polar olefinic monomers of the present invention include, for example, unbranched aliphatic olefins having from 2 to 12 carbon atoms, branched aliphatic olefins having from 4 to 12 carbon atoms, unbranched and branched aliphatic α-olefins having from 2 to 12 carbon atoms, conjugated olefins having 4 to 12 carbon atoms, aromatic olefins having from 8 to 20 carbons, unbranched and branched cycloolefins having 3 to 12 carbon atoms, unbranched and branched acetylenes having 2 to 12 carbon atoms, and combinations thereof. A non-exhaustive list of examples of non-polar olefinic monomers of the present invention includes ethylene, propene, 1-butene, 1-hexene, butadiene, 1,5-hexadiene, isoprene, styrene, alpha-methylstyrene, cyclohexene, cyclohexadiene, norbornene, alkyl-substituted norbornenes, aryl-subsituted norbornenes, norbornadiene, divinylbenzene, acetylene, diacetylene, and alkynylbenzene.

Polar olefinic monomers of the present invention include ethylenically unsaturated monomers having from 2 to 60 carbon atoms and at least one atom such as O, N, B, Al, S, P, Si, F, Cl, Br, and combinations thereof. These polar olefinic monomers include, for example: $C_1$-$C_{22}$ linear or branched chain alkyl(meth)acrylates, bornyl(meth)acrylate, and isobornyl (meth)acrylate; hydroxyethyl(meth)acrylate, hydroxypropyl(meth)acrylate; (meth)acrylamide or substituted (meth)acrylamides; epoxy containing (meth)acrylates such as glycidyl (meth)acrylate; styrene or substituted styrenes; butadiene; vinyl acetate or other vinyl ester; vinyl chloride; vinylidene chloride; vinylidene fluoride; N-butylaminoethyl(meth)acrylate, N,N-di(methyl)aminoethyl (meth)acrylate; monomers containing α,β-unsaturated carbonyl functional groups such as fumarate, maleate, cinnamate and crotonate; and (meth)acrylonitrile. Acid-functional methacrylic monomers include, for example, (meth)acrylic acid, itaconic acid, crotonic acid, phosphoethyl(meth)acrylate, sulfoethyl(meth)acrylate, 2-acrylamido-2-methyl-1-propanesulfonic acid, fumaric acid, maleic anhydride, monomethyl maleate, and maleic acid. The polar olefinic monomer of the present invention may be any monomer containing a polar group, including fluorine-containing monomers and silicon-containing monomers. Further non-exhaustive lists of polar olefinic monomer are disclosed in U.S. patent application no. US 2005/0043494 A1

Multi-ethylenically unsaturated monomers of the present invention may be incorporated into the addition polymer of the present invention to provide crosslinking either during polymerization, or subsequent to polymerization, or both. Multi-ethylenically unsaturated monomers may be polar olefinic or non-polar olefinic monomers, and the ethylenically unsaturated groups may be identical or different. Useful (meth)acrylic multi-ethylenically unsaturated monomers include, but are not limited to, allyl(meth)acrylate, diallyl phthalate, 1,4-butylene glycol di(meth)acrylate, 1,6-hexanediol di(meth)acrylate, and 1,1,1-trimethylolpropane tri (methyl)acrylate.

In the method of polymerizing of the present invention, the neutral metal-pair complex can be used to polymerize: one or more "non-polar olefinic monomers"; one or more "polar olefinic monomers"; or combinations of one or more non-polar olefinic monomers and one or more polar olefinic monomers to form the addition polymer of the present invention. The number average molecular weight, Mn, of the addition polymer of the present invention is: at least 500, at least 1,000, at least 10,000, or at least 20,000; and no more than 5,000,000, no more than 1,000,000, no more than 500,000, or no more than 200,000. The polydispersity of the MWD of the addition polymer of the present invention is: at least 1.000, at least 1.001, at least 1.01, or at least 1.05; and no more than 10, no more than 2.5, no more than 1.5, or no more than 1.1. The MWD of the addition polymer of the present invention may be unimodal or multi-modal, wherein multi-modal includes bimodal and trimodal, as well as higher degrees of modality, and wherein the polydispersity of the MWD for each mode may have the upper and lower limits defined supra.

In the method of polymerizing of the present invention, the neutral metal-pair complex may be usefully employed without co-catalyst, or may be used with a "neutral co-catalyst" (interchangeably referred to as "co-catalyst" herein) capable of accepting an electron pair from the neutral metal-pair complex to from a "neutral adduct". Neutral co-catalysts include, for example, neutral Lewis acids based upon aluminum, boron, and lanthanides. Scandium containing neutral Lewis acids are also useful neutral co-catalysts in the present invention. A non-exhaustive list of neutral co-catalysts includes neutral trisubstitued aluminum compounds, such as, for example: trialkyl aluminum compounds, triaryl aluminum compounds, alkyl aryl aluminum compounds, aralkyl aluminum compounds, alkaryl aluminum compounds, aluminum halides; triaryl boron compounds, alkaryl boron compounds; neutral lanthanide compounds substituted with alkyl groups, aryl groups, and mixtures of both; and scandium compounds substituted with alkyl groups, aryl groups, and mixtures of both. Illustrative examples of aluminum compounds include $Al(C_2H_5)_3$, $Al(CH2CH(CH_3)_2)_3$, $Al(C_3H_7)_3$, $Al((CH_2)_3CH_3)_3$, $Al((CH_2)_5CH_3)_3$, $Al(C6F_5)_3$, $Al(C_2H_5)_2Cl$, and $AlCl_3$. Illustrative examples of boron compounds include: trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane, tris(3,4,5-trifluorophenyl)borane, $B(C_6F_5)_3$, other $B(Ar^F)_3$ compounds wherein "$Ar^F$" denotes "fluoroaryl". Scandium triflate is an example of a scandium cocatalyst useful in the present invention. Both stoichiometric and non-stoichiometric quantities of co-catalyst are usefully employed in the present invention, as are mixtures of co-catalysts. Chemically and structurally useful co-catalysts will be apparent to those skilled in the art based on their respective chemical structures and activities in preparing neutral metal-pair complexes. Alkyl groups typically include 1 to about 24 carbon atoms. The alkyl groups can be cyclic (e.g., cycloalkyl, alkyl-substituted cycloalkyl, or cycloalkyl-substituted alkyl groups) or acyclic, linear or branched chain alkyl groups. Aryl containing groups can include a single aromatic ring, or multiple rings. Alkyl and aryl groups may be substituted with halogen atoms, or other heteroatoms and functional groups, with the proviso that those heteroatoms and functional groups do not interfere with the ability of the co-catalyst to act as a neutral Lewis acid.

The "poly(non-polar olefin)" of the present invention is any polymer including, as polymerized units, any non-polar olefinic monomer capable of insertion addition polymerization in the presence of the neutral metal-pair complex of the present invention. (e.g., polyethylene, polynorbornene, and copolymers with other non-polar olefins).

The "poly(polar olefin)" of the present invention is any polymer including, as polymerized units, any polar olefin capable of insertion addition polymerization in the presence of the neutral metal-pair complex of the present invention (e.g., poly[(meth)acrylates], poly[vinylidene halide(s)], and related copolymers).

A "poly[(polar olefin)-(non-polar olefin)]" of the present invention is any polymer including, as polymerized units, at least one non-polar olefinic monomer and at least one polar olefinic monomer capable of insertion addition polymerization in the presence of the neutral metal-pair complex of the present invention. The following is short, non-exhaustive, list of illustrative examples of poly[(polar olefin)-(non-polar olefin) which copolymers: poly[ethylene-co-methyl(meth)acrylate], poly[octene-co-methyl(meth)acrylate], poly[propylene-co-(meth)acrylate], poly[norbornene-co-(meth)acrylate]. In fact, the poly[(polar olefin)-(non-polar olefin)] may include any polar olefin and any non-polar olefin capable of insertion addition polymerization in the presence of the neutral metal-pair complex of the present invention. The molar ratio of polar olefinic monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention is a copolymer, that copolymer may include, as polymerized units, two, three, four, or more than four different monomers, with no particular limit to the number of different monomers. For example, in one embodiment of the present invention, the poly[(polar olefin)-(non-polar olefin)] is a terpolymer including, as polymerized units, norbornene, 1-octene, and methyl acrylate.

When at least one polar monomer polymerized by the method of the present invention to form a "poly[(polar olefin)-(non-polar olefin)]" is a (meth)acrylate monomer, the molar ratio of (meth)acrylate monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

Further, when both polar olefinic monomers and non-polar olefinic monomers are polymerized together in the polymerization method of the present invention, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

In particular, when both polar olefinic monomers and non-polar olefinic monomers are polymerized together in the polymerization method of the present invention, and at least one of the polar olefinic monomers is a (meth)acrylate monomer, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

Still further, when the addition polymer of the present invention is a poly(polar olefin) and at least one of the polar olefinic monomers, incorporated as polymerized units, is a (meth)acrylate monomer, the molar ratio of all (meth)acrylate monomers, present as polymerized units, to all non-(meth) acrylate monomers, present as polymerized units, is: at least 0.05:99.95, at least 0.5:99.5, at least 10:90, at least 20:80, or at least 40:60; or no more than 100:0, no more than 99.5:0.5, no more than 90:10, no more than 80:20, or no more than 60:40.

Similarly, when the addition polymer of the present invention is a poly[(polar olefin)-(non-polar olefin)] and at least one of the polar olefinic monomers, incorporated as polymerized units, is a (meth)acrylate monomer, the molar ratio of all (meth)acrylate monomers, present as polymerized units, to all non-(meth)acrylate monomers, present as polymerized units, is: at least at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention includes, as polymerized units, at least one cyclic olefin, incorporated as polymerized units, the molar ratio of all cyclic olefin monomers, present as polymerized units, to all non-(cyclic olefin) monomers, present as polymerized units, is: at least 0.05:99.05, at least 0.5:99.5, at least 10:90, at least 20:80, or at least 40:60; or no more than 100:0, no more than 99.5:0.5, no more than 90:10, no more than 80:20, or no more than 60:40.

Crosslinked polymers can be prepared by copolymerizing norbornene and substituted norbornene monomers with a multifunctional norbornene-type crosslinking monomer. By multifunctional norbornene-type crosslinking monomer is meant that the crosslinking monomer contains at least two norbornene-type moieties (norbornene-type double bonds), each functionality being polymerizable in the presence of the catalyst system of the present invention. The crosslinkable monomers include fused multicyclic ring systems and linked multicyclic ring systems.

The method of preparing the addition polymer of the present invention can be carried out at a reaction temperature (° C.) of: at least −100° C., at least −50° C., at least 0° C., or at least 20° C.; and no more than 200° C., no more than 160° C., no more than 140° C., or no more than 120° C. This method can be carried out at a pressure (in atmospheres, i.e., the pressure inside the reactor is 1.0 atmosphere for a value of 1.0) of: at least 0.01, at least 0.1, at least 0.5, or at least 1.0, and no more than 1,000, no more than 100, no more than 10, or no more than 5. Further, the molar ratio of ethylenically unsaturated monomer to the neutral metal-pair complex of present invention is: at least 50:1, at least 200:1, at least 250:1, or at least 1,000:1, and no more than 5,000,000:1, no more than 2,000,000:1, or no more than 500,000:1, no more than 250,000:1, or no more than 100,000:1. For gaseous monomers at high pressures, in particular constant high pressures, e.g., equal to or greater than 400 psi, the molar ratio of ethylenically unsaturated monomer to the neutral metal-pair complex of present invention may be even higher than 5,000,000:1, for example, no more than 6,000,000:1, no more than 8,000,000:1, or even higher. In the method of polymerization of the present invention, the amount of diluent, expressed as volume (milliliters) of diluent per millimole of the neutral metal-pair complex of the present invention, is: at least 0.0, at least 10, at least 50, or at least 100; and no more than 10,000,000, no more than 1,000,000, no more than 100,000, no more than 10,000, or no more than 5,000.

When particles of the addition polymer are produced by the method of preparing the addition polymer of the present invention, depending on the particular details of that method, the polymer particles have a mean particle diameter (i.e., mean particle size), expressed in microns, of: at least 0.002, at least 0.04, at least 0.1, or at least 0.8; and no more than 500, no more than 20, no more than 10, no more than 5, or no more than 3. The PSD polydispersity of the particles is: at least 1, at least 1.001, at least 1.01, or at least 1.05; and no more than 10, no more than 5, no more than 1, no more than 1.3, or no more than 1.1. The PSD of the addition polymer of the present invention may be unimodal or multi-modal, wherein multi-modal includes bimodal and trimodal, tetramodal, as well as higher degrees of modality, and wherein the polydispersity of the PSD for each particle size mode may have the upper and lower limits defined supra. One skilled in the art of catalytic polymerization will further recognize that it is even possible to prepare particles having a mean particle diameter greater than 1000 microns (1 millimeter). This may happen, for example, as the result of evaporation during or after solution or bulk polymerization, or polymerization involving polymer precipitation. In this way, even larger monolithic polymer structures may be formed.

The method for preparing the addition polymer of the present invention may be carried out in bulk or in a diluent. If the catalytic composition is soluble in the one or more ethylenically unsaturated monomers to be polymerized, it may be convenient to carry out the polymerization in bulk. Such bulk polymerizations may be carried out, for example, in batch or continuous mode, or by reaction injection molding or other extrusion or mold based techniques. In another embodiment of the present invention, the polymerization is carried out in a diluent. Any organic or aqueous diluent which does not adversely interfere with the catalytic composition and is a solvent for the monomers may be employed. Illustrative examples of organic solvents are: aliphatic (non-polar) hydrocarbons, e.g., hexane and heptane; alicyclic hydrocarbons, e.g., cyclohexane; aromatic hydrocarbons, e.g., toluene; halogenated (polar) hydrocarbons, e.g., methylene chloride and chlorobenzene. For polymerization systems in which the catalytic composition is not degraded, the diluent may be water, solvents miscible with water, and combinations thereof. The diluent may further include, for example, any of the fugitive substances disclosed in patent application no. US 2005/0043494 A1 and U.S. Pat. No. 6,632,531, e.g., 2,2-dimethylypropane, 1,1-difluoroethane, 1,1,1,2-tetrafluoroethylene propane (−42.1° C.), carbon dioxide, and tetrafluoromethane (−130° C.), wherein the reaction is carried out under supercritical or below supercritical conditions.

The diluent of the present invention may also be an "ionic liquid" al disclosed in U.S. patent application no. US 2005/0043494 A1. Ionic liquids are either organic salts or mixtures of salts that are fluid at room or near-room temperature as disclosed in Dupont, *J. Chem. Rev.* 2002, 102, 3667; Kabisa, P. *Prog. Poly. Sci.* 2004, 29, 3.

The suitability of a given atmosphere for carrying out any of the reactions of the present invention will depend upon the stability of the reactants, intermediates and by-products to that atmosphere. Typically gases, including nitrogen or argon, for example, are utilized. Choice of atmosphere gases for a given polymerization will be apparent to one of ordinary skill in the art.

When utilized in the preparation of the addition polymer of the present invention, the monomers and/or catalytic composition of the present invention may not be fully soluble, or may even be insoluble, in the diluent. This situation might, for example, occur in heterogeneous systems wherein the locus of polymerization must be accessed by both catalytic composition and ethylenically unsaturated monomer. In such cases, it may be advantageous to employ one or more transport agents to transport monomers, or the complexes of the catalytic composition, to the desired locus of polymerization. For example, transport agents such as cyclodextrins may be advantageously employed to transport ethylenically unsaturated monomers having low, or very low, water solubility, across the aqueous phase to polymer particles during aqueous emulsion polymerization.

In addition to being carried out as bulk and solution polymerizations, the polymerizations of the present reaction can be carried out in the gas phase in, for example fluidized bed or stirred tank reactors, optionally in the presence of prepolymer for control of the size and shape of polymers formed. Polyethylene, polybutene, polyhexene, and related copolymers, including copolymers containing, for example, methyl methacrylate may be prepared by gas phase polymerization.

A still further method for producing the addition polymer of the present invention may be any appropriate method known to the art, including, but not limited to aqueous solution polymerization, aqueous emulsion polymerization, aqueous suspension polymerization, aqueous microemulsion polymerization, aqueous mini-emulsion, aqueous inverse emulsion polymerization, aqueous dispersion polymerization, and aqueous precipitation polymerization. Descriptions of emulsion polymerization methods are disclosed in Blackley, D. C. *Emulsion Polymerisation*; Applied Science Publishers: London, 1975; Odian, G. *Principles of Polymerization*; John Wiley & Sons: New York, 1991; *Emulsion Polymerization of Acrylic Monomers*; Rohm and Haas, 1967. The method of the present invention further includes methods disclosed in U.S. Pat. No. 6,632,531, and published U.S. patent application US2003/0007990.

The neutral metal-pair complex of the present invention is suitably employed as an unsupported material. Alternatively, any of the complexes of the present invention may be supported on an "inorganic solid carrier" ("inorganic carrier") or an "organic polymeric solid catalyst carrier" ("organic carrier") which is normally solid under reaction conditions and is substantially insoluble in the reaction medium. Used herein, the terms "carrier" and "support" are used interchangeably. Illustrative of suitable inorganic carriers are inorganic acidic oxides such as alumina and inorganic materials known as refractory oxides. Suitable refractory oxides include synthetic components as well as acid treated clays and similar materials such as kieselguhr or crystalline macroreticular aluminosilicates known in the art as molecular sieves. In general, synthetic catalyst carriers are preferred over natural occurring materials or molecular sieves. Exemplary synthetic catalyst carriers include alumina, silica-alumina, silica-magnesia, silica-alumina-titania, silica-alumina-zirconia, silica-titania-zirconia, silica-magnesia-alumina, magnesium chloride, and the like. Organic carriers include, for example, macroreticular resins which may, or may not, bear polar functional groups or carbon-carbon double bonds.

When the neutral metal-pair complex of the present invention is supported, its proportion to carrier is not critical. In general, proportions of neutral metal-pair complex, or precursor complex of the present invention, in percent by weight, based on the catalyst carrier, are: at least 0.001%, at least 0.01%, at least 0.1%, or at least 1.0%; and no more than 5%, no more than 10%, no more than 20%, or no more than 70%. The neutral metal-pair complex is introduced onto the carrier in any suitable manner. In one modification, the supported neutral metal-pair complex is prepared by intimately contacting the preformed neutral metal-pair complex and the carrier in an inert diluent, which may or may not be the same inert diluent employed for preparing the neutral metal-pair complex. In another modification, the neutral metal-pair complex can be prepared directly on the catalyst carrier support surface by contacting the neutral metal-pair complex precursors in the presence of the catalyst carrier in a suitable inert diluent. In addition to the supports enumerated supra, the neutral metal-pair complex of the present invention can be supported on any of the supports or matrices disclosed in published U.S. patent applications US2002/60226997, US2002/0052536, in U.S. patent applications U.S. 60/383,650 and U.S. 60/440,142, and in Chen and Marks, *Chem. Rev.*, 100, 1391-1434, 2000.

In one embodiment of the method of the present invention for preparing a neutral metal-pair complex, a first precursor complex with a second precursor complex are combined in the following reaction scheme:

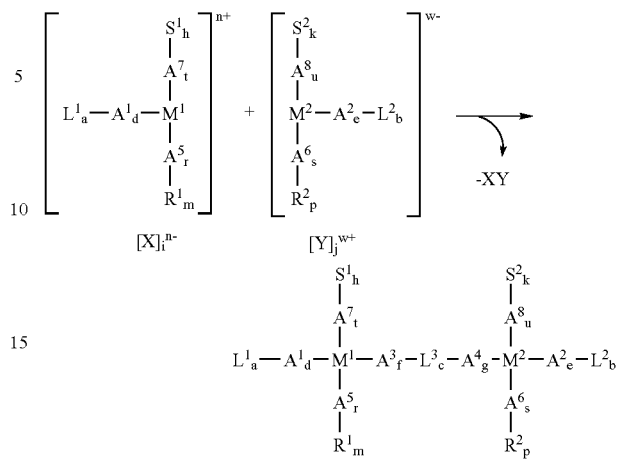

A first precursor complex (containing $M^1$) is contacted with a second precursor (a complex containing $M^2$) to form a neutral metal-pair complex. The first precursor may be a neutral complex (n=0), or a cationic metal complex (n=1, 2, or 3), i.e., having positive charge, accompanied by a set of one or more anionic counter ions having a combined negative charge which balances the charge on the cationic metal complex (i.e., if n=2 for the cationic metal complex, then n=2 for the combined charge of the set of anionic counter ions. Conversely, the second precursor may be a neutral complex (w=0), or an anionic metal complex (w=1, 2, or 3), i.e., having negative charge, accompanied by a set of one or more cationic counter ions having a combined positive charge which balances the charge on the anionic metal complex (i.e., if w=2 for the anionic metal complex, then w=2 for the combined charge of the set of cationic counter ions.

It may further be desirable that a "scavenger" be present during the reaction of a first precursor complex with a second precursor complex. A scavenger of the present invention is a Lewis Acid capable or displacing a first ligand from a coordination site of first metal atom, $M^1$, of a first precursor complex, rendering that coordination site open to formation of a coordination bond with a donor a second precursor complex. A illustrative list of scavengers includes, but is not limited to, bis(cyclooctadiene)nickel, acetylacetonatobis(ethylene)rhodium, tripentafluorophenylborane, triisobutylaluminum, triethylaluminum, and combinations thereof.

The temperature (° C.) for the reaction generating the neutral metal-pair complex is: at least −100° C., at least −50° C., at least 0° C., or at least 20° C.; and no more than 200° C., no more than 160° C., no more than 140° C., or no more than 120° C. In the method of preparation of the neutral metal-pair complex of the present invention, the amount of diluent, expressed as volume (milliliters) pre millimole of neutral metal-pair complex, is: at least 0.0, at least 2, at least 5, or at least 10; and no more than 1,000, no more than 500, no more than 200, or no more than 100. Useful diluents include any of the non-aqueous diluents (vide supra) useful in carrying out the polymerization of the ethylenically unsaturated monomers of the present invention. In cases in which neither the precursor complex nor the neutral metal-pair complex is adversely affected, water or water miscible diluents may be utilized as well.

In another embodiment of the method of preparing the neutral metal-pair complex of the present invention, any of the preceding reaction schemes may be carried out in the presence of an inorganic support, an organic polymeric support, a pair-coupling moiety, or a combination thereof.

The addition polymers prepared using the catalytic composition of the present invention afford many new products and market opportunities currently unachievable in a broad spectrum of market segments, a short, non-exhaustive list of which includes coatings, free-standing films, plastics additives, inks, adhesives and sealants, textiles, composites, and electronics materials. (See also those applications for the addition polymers of the present invention which are disclosed in U.S. patent application no. US 2005/0043494 A1).

Various embodiments of the present invention will now be described in detail in the following Examples. Chemicals used in the Examples are listed in Table I.

TABLE II

Chemicals used in the examples.

| Chemical (purity) | Source | CAS # |
|---|---|---|
| Chlorobenzene | Aldrich | 108-90-7 |
| Methylene Chloride (99+%) | Aldrich | 75-09-2 |
| Hexanes (98+) | Aldrich | 73513-42-5 |
| Hexafluoroisopropanol norbornene, 5-R-NB (R = CH$_2$C(CF$_3$)$_2$OH) | | 196314-61-1 |
| Q-5 oxygen scavenger | Engelhard, Iselin, NJ 08830 | |
| Tricyclohexylphosphine (97%) | Strem | 2622-14-2 |
| Ni(cod)$_2$ (Bis(1,5-cyclooctadiene)nickel (0), 98+ %) | Strem | 1295-35-8 |
| Rh(acac)(C$_2$H$_4$)$_2$ (Acetylacetonatobis(ethylene)rhodium (I), 99%) | Strem | 12082-47-2 |
| B(C$_6$F$_5$)$_3$ (tris(pentafluorophenyl)borane) | Boulder Scientific | 1109-15-5 |
| Na$_2$S (sodium sulfide) | Aldrich | 1313-82-2 |
| KB(C$_6$F$_5$)$_4$ (potassium tetrakispentafluorophenylborate) | Boulder Scientific | 89171-23-3 |

General procedures. The polymerization reactions of Examples 1-14 are carried out in a dry box under a nitrogen atmosphere. After the reaction is set up, the glass vessel is sealed, removed from the dry box, and heated using water bath/Variomag heat block in a fume hood. Unless otherwise noticed, all chemicals are purchased from the supplier and used without further purification. Nitrogen is purified by passage through columns containing activated molecular sieves and Q-5 oxygen scavenger. Toluene is purified by passage through columns of activated molecular sieves (4 Å)/alumina/O$_2$ remover (e.g., Q-5) and methylene chloride is purified by passage through columns of activated alumina. Methyl acrylate (99%) is purchased from Aldrich and purified by passage through columns of MEHQ inhibitor remover and activated molecular sieves (4 Å), and purged with nitrogen for 0.5 hour. Norbornene (99%) is purchased from Acros and purified using one of the following two methods: 1) It is dried with calcium hydride at 60° C. overnight, degassed by freeze-pump-thaw twice and vacuum transferred at 50° C. to a dry glass receiver; 2) It is dissolved in a small amount of toluene to yield a clear colorless solution, which is passed through a column of activated molecular sieves (4 Å) and purged with nitrogen for 0.5 hour. The concentration of this toluene solution of norbornene is determined by $^1$H NMR analysis. Hexafluoroisopropanol norbornene and chlorobenzene are each sparged with nitrogen for 0.5 hours and then purified by passage over a column containing alumina and molecular sieves (3 Å).

Nuclear Magnetic Resonance (NMR) Spectroscopy. NMR spectra are recorded on Varian 600, Bruker DMX-400 or DRX-500 spectrometers at 23° C. unless otherwise indicated. $^1$H and $^{13}$C chemical shifts are reported vs. SiMe$_4$ and are determined by reference to residual $^1$H and $^{13}$C solvent signals.

Molecular Weight Determination using Gel Permeation Chromatography (GPC). Gel Permeation Chromatography, otherwise known as Size Exclusion Chromatography (SEC), actually separates the members of a distribution of polymer chains according to their hydrodynamic size in solution rather than their molar mass. The system is then calibrated with standards of known molecular weight and composition to correlate elution time with molecular weight. The techniques of GPC are discussed in detail in Modern Size Exclusion Chromatography, W. W. Yau, J. J Kirkland, D. D. Bly; Wiley-Interscience, 1979, and in A Guide to Materials Characterization and Chemical Analysis, J. P. Sibilia; VCH, 1988, p. 81-84.

All samples are prepared at concentration 2 mg/mL in THF or chloroform (HPLC grade) and gently stirred to dissolve the polymer sample completely. All polymer solutions are filtered using 1 μm PTFE filter. GPC separation are performed using 2 PL gel Mixed B columns and evaporative light scattering detector (ELSD). Typical chromatographic conditions: 2 PL gel MIXED B columns, particle size 5 μm; eluent: THF or CHCl$_3$ (HPLC grade), 1.0 ml/min; injected volume of sample solution: 50 μL; PS standards with molecular weight ranging from 580 to 2 560 000 g/mol (0.5 mg/mL in THF or CHCl$_3$) are used to construct calibration curve; ELS detection, (TN=40° C., TECH=80° C., Fnitrogen=1 L/min).

Liquid Chromatography—NMR. Typical LC-NMR experiment conditions: a sample is dissolved in CDCl$_3$ to form a solution (ca. 1%) and filtered through a 0.2 micron filter. The polymer separation is carried out on a SUPLECO-SIL reverse-phase C-18 column (25 cm×4.6 mm), with a flow rate of 1 ml/min. The Evaporative Light Scattering detection (ELSD) and UV detectors are employed with a solvent gradient of acetonitrile/water/THF from 95/5/0 to 0/0/100 in 24 minutes. $^1$H LC-NMR spectra are acquired on a Varian UNITY INOVA 600 MHz NMR spectrometer.

Differential Scanning Calorimetry (DSC): Modulated Differential Scanning Calorimetry measurements are carried out on a Q-1000 Series DSC made by TA Instruments. Samples are run under an inert atmosphere of nitrogen at a flow rate of 25 mL/min. Samples are heated from −90° C. to +380° C. at a rate of 7° C./min with a modulation amplitude of 1° C. and a period of 40 s.

The following neutral metal-pair complexes are utilized in the examples:

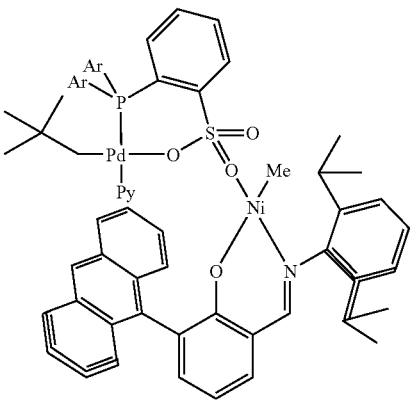

Py = C$_6$H$_5$N
Ar = 2-MeOC$_6$H$_4$

Neutral Metal-Pair Complex I

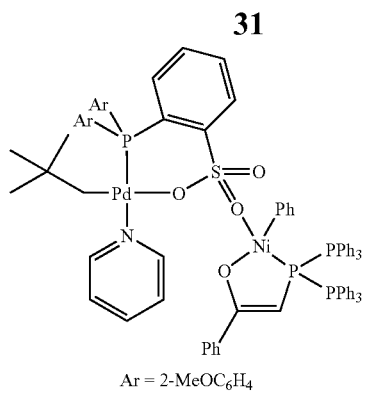
Ar = 2-MeOC$_6$H$_4$
Neutral Metal-Pair Complex II
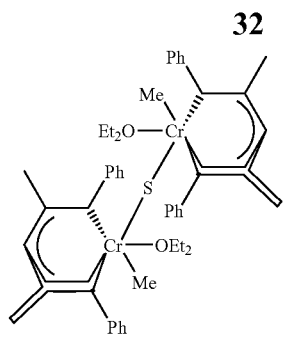
Neutral Metal-Pair Complex VI
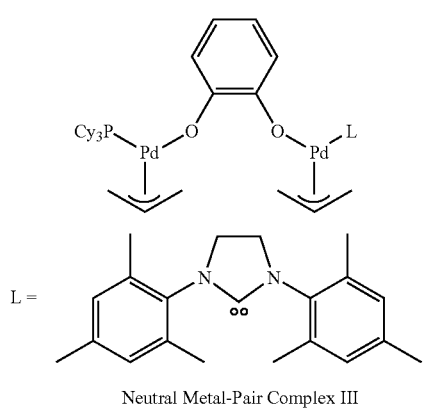
Neutral Metal-Pair Complex III
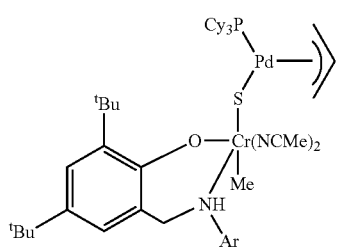
Ar = 2,6-Me$_2$—Ph
Neutral Metal-Pair Complex VII
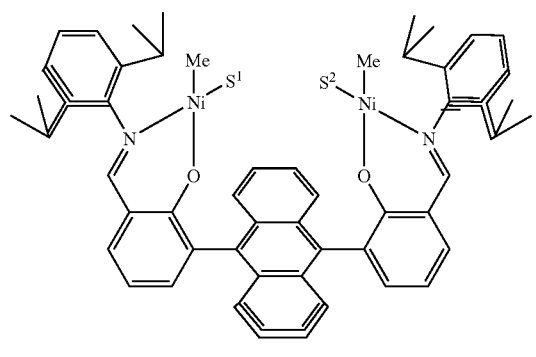
S$^1$ = S$^2$ = CH$_3$CN
Neutral Metal-Pair Complex IV
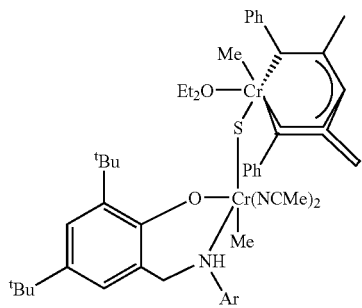
Ar = 2,6-Me$_2$—Ph
Neutral Metal-Pair Complex VIII
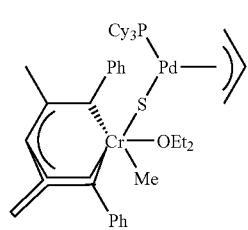
Neutral Metal-Pair Complex V
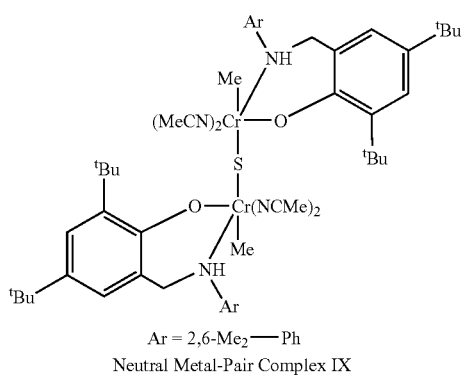
Ar = 2,6-Me$_2$—Ph
Neutral Metal-Pair Complex IX The following complexes are utilized in the preparation of the above neutral metal-pair complexes.

Complex W
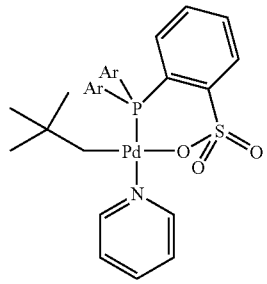
Ar = 2-MeOC₆H₄

Complex X
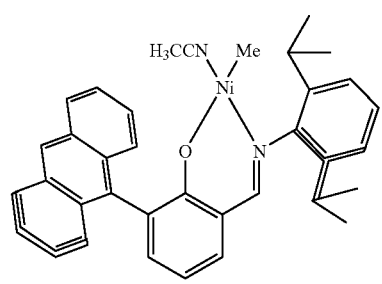

Complex E
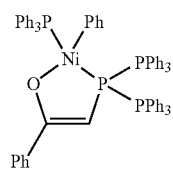

Complex G
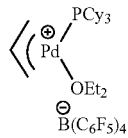

Complex N
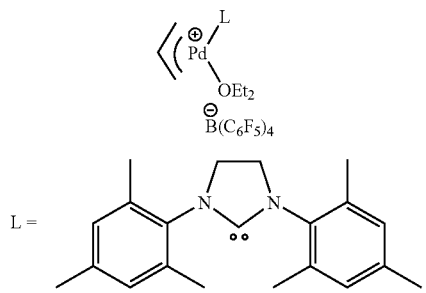

Complex F
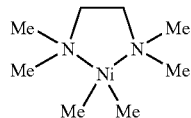

Complex Y
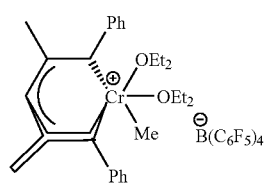

Complex B
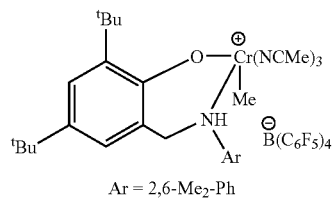
Ar = 2,6-Me₂-Ph

Complex O
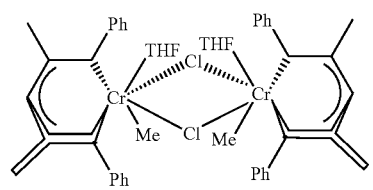

sal-An-sal
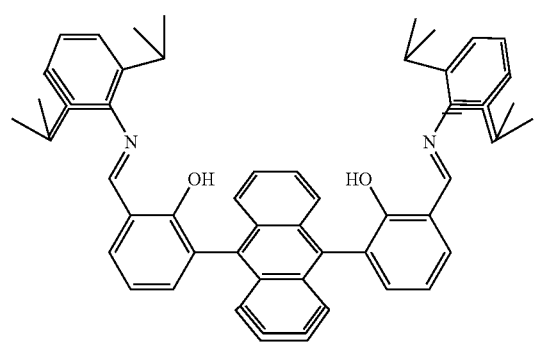

Examples of preparations of neutral metal-pair complexes are described below.

EXAMPLE A

Synthesis of Neutral Metal-Pair Complex I (Scheme 1)

Precursor Complex W + Precursor Complex X ⟶ Neutral Metal-Pair Complex I        (1)

A 50 mL Schlenk flask is charged with Complex W (20 mmol). CH₂Cl₂ (10 mL) is added to form a clear yellow solution. A solution of Complex X (20 mmol) in CH₂Cl₂ (5 mL) is added by syringe at 0° C. to form a dark yellow solution. The reaction mixture is stirred at 0° C. for 60 min, and then CH₂Cl₂ (approximately 10 mL) is removed under vacuum. The concentrated solution is allowed to sit at −80° C. to yield yellow crystalline solid overnight, which are isolated by filtration. The experiment should afford a yellow solid (yield: 82.2%). NMR spectra should reveal that the product is Neutral Metal-Pair Complex I.

EXAMPLE B

Synthesis of Neutral Metal-Pair Complex II (Scheme 2)

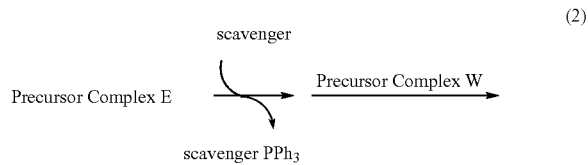

(2)

A 50 mL Schlenk flask is charged with Complex E (20 mmol) and equal molar amount of scavenger such as Ni(cod)$_2$ (or B(C$_6$F$_5$)$_3$, Rh(acac)(C$_2$H$_4$)$_2$). CH$_2$Cl$_2$ (10 mL) is added at −40° C. to form a clear dark yellow solution. A solution of Complex W (20 mmol) in CH$_2$Cl$_2$ (5 mL) is added by syringe also at −40° C. to form a bright yellow solution. The reaction mixture is stirred at −40° C. for 60 min, and then CH$_2$Cl$_2$ (approximately 10 mL) is removed under vacuum. The concentrated solution is allowed to sit at −80° C. to yield yellow crystalline solid overnight, which are isolated by filtration. The experiment should afford a yellow solid (yield: 77%). NMR spectra should reveal that the product is Neutral Metal-Pair Complex II.

EXAMPLE C

Synthesis of Neutral Metal-Pair Complex III (Scheme 3)

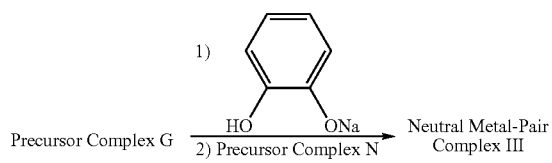

(3)

A 50 mL Schlenk flask is charged with Complex G (20 mmol) and ortho-(HO)C$_6$H$_4$(ONa) (20 mmol). CH$_2$Cl$_2$ (10 mL) is added at ambient temperature to form a clear pale yellow solution. A solution of Complex N (20 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is topped with a layer of pentane (ca. 5 mL) and is allowed to sit at ambient temperature overnight to yield yellow crystalline solid, which are isolated by filtration. The experiment should afford a yellow solid (yield: 79.9%). NMR spectra should reveal that the product is Neutral Metal-Pair Complex III.

EXAMPLE D

Synthesis of Neutral Metal-Pair Complex IV (Scheme 4)

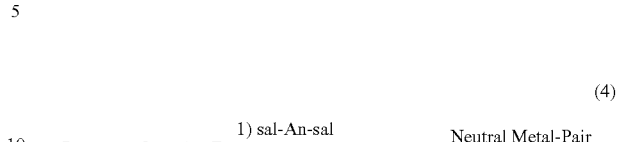

(4)

A 50 mL Schlenk flask is charged with Complex F (25 mmol) and sal-An-sal (25 mmol). CH$_3$CN (15 mL) is added at ambient temperature, which is followed by the addition of a solution of Complex F in CH$_3$CN (25 mmol, 10 mL). The reaction mixture is stirred at ambient temperature for 30 min, and then CH$_3$CN is removed under vacuum, which should afford a yellow solid (yield 77.8%). NMR spectra should reveal that the product is Neutral Metal-Pair Complex IV.

EXAMPLE E

Synthesis of Neutral Metal-Pair Complex V (Scheme 5)

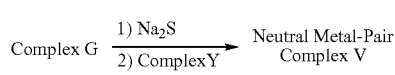

(5)

A 50 mL Schlenk flask is charged with Complex G (30 mmol) and Na$_2$S (30 mmol). CH$_2$Cl$_2$ (10 mL) is added at ambient temperature to form a clear pale yellow solution. A solution of Complex Y (30 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is allowed to sit at −80° C. to yield yellow crystalline solid overnight, which are isolated by filtration. The experiment should afford a yellow solid (yield: 79.9%). NMR spectra should reveal that the product is Neutral Metal-Pair Complex V.

EXAMPLE F

Synthesis of Neutral Metal-Pair Complex VI (Scheme 6)

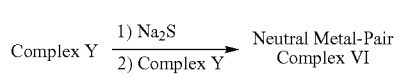

(6)

A 50 mL Schlenk flask is charged with Complex Y (30 mmol) and Na$_2$S (30 mmol). CH$_2$Cl$_2$ (10 mL) is added at ambient temperature to form a clear pale yellow solution. A solution of Complex Y (30 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is allowed to sit at −80° C. to yield yellow crystalline solid overnight, which are isolated by filtration. The experiment should afford a yellow solid (yield: 77.8%). NMR spectra should reveal that the product is Neutral Metal-Pair Complex VI.

EXAMPLE G

Synthesis of Neutral Metal-Pair Complex VII (Scheme 7)

(7)

A 50 mL Schlenk flask is charged with Complex G (30 mmol) and Na$_2$S (30 mmol). CH$_2$Cl$_2$ (10 mL) is added at ambient temperature to form a clear pale yellow solution. A solution of Complex B (30 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is allowed to sit at −80° C. to yield yellow crystalline solid overnight, which are isolated by filtration. The experiment should afford a yellow solid (yield: 77.1%). NMR spectra should reveal that the product is Neutral Metal-Pair Complex VII.

EXAMPLE H

Synthesis of Neutral Metal-Pair Complex VIII (Scheme 8)

(8)

A 50 mL Schlenk flask is charged with Complex Y (30 mmol) and Na$_2$S (30 mmol). CH$_2$Cl$_2$ (10 mL) is added at ambient temperature to form a clear pale yellow solution. A solution of Complex B (30 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is allowed to sit at −80° C. to yield yellow crystalline solid overnight, which are isolated by filtration. The experiment should afford a yellow solid (yield: 82.2%). NMR spectra should reveal that the product is Neutral Metal-Pair Complex VIII.

EXAMPLE I

Synthesis of Neutral Metal-Pair Complex IX (Scheme 9)

(9)

A 50 mL Schlenk flask is charged with Complex B (30 mmol) and Na$_2$S (30 mmol). CH$_2$Cl$_2$ (10 mL) is added at ambient temperature to form a clear pale yellow solution. A solution of Complex B (30 mmol) in CH$_2$Cl$_2$ (15 mL) is added by syringe at ambient temperature to form a yellow solution. The reaction mixture is stirred at ambient temperature for 60 min, and then CH$_2$Cl$_2$ (approximately 30 mL) is removed under vacuum. The concentrated solution is allowed to sit at −80° C. to yield yellow crystalline solid overnight, which are isolated by filtration. The experiment should afford a yellow solid (yield: 89.8%). NMR spectra should reveal that the product is Neutral Metal-Pair Complex IX.

EXAMPLE J

Synthesis of Complex Y (Scheme 10)

(10)

A 250 mL Schlenk flask is charged with Complex 0 (100 mmol) and KB(C$_6$F$_5$)$_4$ (200 mmol). A mixed solvent of CH$_2$Cl$_2$ (50 mL) and diethyl ether (Et$_2$O, 25 mL) is added at 0° C. to form a white slurry in a pale yellow solution. The reaction mixture is stirred at 0° C. for 120 min. KCl is removed by filtration. Solvent (approximately 60 mL) is removed under vacuum. The concentrated solution is allowed to sit at −80° C. to yield yellow crystalline solid overnight, which are isolated by filtration. The experiment should afford a yellow solid (yield: 91.2%). NMR spectra should reveal that the product is Complex Y.

Examples of polymerizations by neutral metal-pair complexes are described below.

EXAMPLE 1

Utilizing a neutral metal-pair complex to prepare a homopolymer of norbornene, according to the method of the present invention. A 100 mL serum bottle is charged with toluene (20 mL) and norbornene (1. 13 g, 12 mmol, pre-dissolved in toluene, 86 wt %) and sealed with a rubber septum. A solution of Neutral Metal-Pair Complex I (0.1 μmol) in CH$_2$Cl$_2$ (1 mL) is added by syringe at 50° C. The reaction mixture is stirred at 50° C. for 1 hour, which is then cooled to ambient temperature and quenched with methanol (50 mL) to yield an off-white slurry. The solid is isolated by filtration, washed with fresh methanol (3×15 mL) and dried under vacuum at 60° C. overnight, which should yield an off-white solid (0.95 g). NMR analysis should reveal that the product is polynorbornene. GPC analysis should reveal a unimodal pattern: Mw 1200000, Mn 1000000, Mw/Mn 1.2.

EXAMPLE 2

Utilizing a neutral metal-pair complex to prepare a homopolymer of ethylene, according to the method of the present invention. Toluene (3 mL) is charged to the glass liner of a steel pressure vessel (8 mL capacity) equipped with a mechanical stirrer. The pressure vessel is sealed and heated to 50° C. Ethylene pressure (350 psig) is introduced. Neutral Metal-Pair Complex II (8 μmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 2 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. The melting transitions measured by Differential Scanning Calorimetry (DSC) should be about 130° C. and the heat of fusion ($\Delta H_f$) should be greater than 100 J/g.

EXAMPLE 3

Utilizing a neutral metal-pair complex to prepare a homopolymer of methyl acrylate, according to the method of the present invention. A 100 mL serum bottle is charged with toluene (20 mL) and methyl acrylate (8.6 g, 0.1 mol) and sealed with a rubber septum. A solution of Neutral Metal-Pair Complex III (10 μmol) in $CH_2Cl_2$ (1 mL) is added by syringe at 50° C. The reaction mixture is stirred at 50° C. for 4 hours and then cooled to ambient temperature and quenched with methanol (100 mL). The precipitated polymer is isolated by filtration, washed with fresh methanol (3×25 mL) and dried under vacuum at 65° C. overnight, which should yield a white solid (1.2 g). NMR analysis should reveal that the product is poly(methyl acrylate). GPC analysis should reveal a unimodal pattern: Mw 100000, Mn 58000, Mw/Mn 1.7.

EXAMPLE 4

Utilizing a neutral metal-pair complex to prepare a homopolymer of styrene, according to the method of the present invention. A 100 mL serum bottle is charged with toluene (20 mL) and styrene (10.4 g, 0.1 mol) and sealed with a rubber septum. A solution of Neutral Metal-Pair Complex IV (10 μmol) in $CH_2Cl_2$ (1 μL) is added by syringe at 50° C. The reaction mixture is stirred at 50° C. for 4 hours and then cooled to ambient temperature and quenched with methanol (100 μL). The precipitated polymer is isolated by filtration, washed with fresh methanol (3×25 mL) and dried under vacuum at 65° C. overnight, which should yield a white solid (5 g). NMR analysis should reveal that the product is polystyrene. GPC analysis should reveal a unimodal pattern: Mw 250000, Mn 125000, Mw/Mn 2.0.

EXAMPLE 5

Utilizing a neutral metal-pair complex to prepare a homopolymer of vinyl acetate, according to the method of the present invention. A 100 mL serum bottle is charged with toluene (20 mL) and vinyl acetate (8.6 g, 0.1 mol) and sealed with a rubber septum. A solution of Neutral Metal-Pair Complex V (10 μmol) in $CH_2Cl_2$ (1 mL) is added by syringe at 50° C. The reaction mixture is stirred at 50° C. for 4 hours and then cooled to ambient temperature and quenched with methanol (100 mL). The precipitated polymer is isolated by filtration, washed with fresh methanol (3×25 mL) and dried under vacuum at 65° C. overnight, which should yield a white solid (2.0 g). NMR analysis should reveal that the product is poly(vinyl acetate). GPC analysis should reveal a unimodal pattern: Mw 170000, Mn 86000, Mw/Mn 2.0.

EXAMPLE 6

Utilizing a neutral metal-pair complex to prepare a homopolymer of vinyl chloride, according to the method of the present invention. A Fischer-Porter reactor is charged with toluene (10 mL). Vinyl chloride (89 mmol, measured by a 800-mL glass bulb) is added by condensation at −196° C. The reactor is gradually warmed to −78° C. and Neutral Metal-Pair Complex VI (0.6 μmol) in $CH_2Cl_2$ (1 mL) is added by a syringe through a rubber septum. The reactor is sealed and gradually warmed to 55° C., at which temperature the reaction mixture is vigorously stirred. 6 hours later, the reactor is cooled to ambient temperature an excess pressure is released before the reaction mixture is poured into a beaker containing acidified methanol (1 v/v %, 250 mL) to yield a white slurry. The solid is collected by filtration, washed with fresh methanol (3×15 mL) and dried under vacuum at 60° C. for 18 hours, which should yield a white solid (4.8 g). NMR analysis should reveal that the product is poly(vinyl chloride). GPC analysis should reveal a unimodal pattern: Mw 220000, Mn 200000, Mw/Mn 1.1.

EXAMPLE 7

Utilizing a neutral metal-pair complex to prepare a homopolymer of methyl vinyl ether, according to the method of the present invention. A 100 mL serum bottle is charged with toluene (20 mL) and methyl vinyl ether (5.8 g, 0.1 mol, pre-dissolved in toluene, 74 wt %) and sealed with a rubber septum. A solution of Neutral Metal-Pair Complex VII (0.25 μmol) in $CH_2Cl_2$ (1 mL) is added by syringe at 50° C. The reaction mixture is stirred at 50° C. for 4 hours, which is then cooled to ambient temperature and quenched with methanol (100 mL) to yield a white slurry. The solid is isolated by filtration, washed with fresh methanol (3×25 mL) and dried under vacuum at 65° C. overnight, which should yield a white solid (5.1 g). NMR analysis should reveal that the product is poly(methyl vinyl ether). GPC analysis should reveal a unimodal pattern: Mw 140000, Mn 100000, Mw/Mn 1.4.

EXAMPLE 8

Utilizing a neutral metal-pair complex to prepare a copolymer of 5-R-norbornene ($R=CH_2C(CF_3)_2(OH)$) and tert-butyl acrylate, according to the method of the present invention. The 100 mL serum bottle is charged with toluene (25 μL), 5-R-norbornene (13.7 g, 50 mmol), tert-butyl acrylate (6.4 g, 50 mmol), and sealed under $N_2$ with a rubber septum. A solution of Neutral Metal-Pair Complex VIII (0.15 μmol) in $CH_2Cl_2$ is added by syringe at 50° C. The reaction mixture is stirred at 50° C. 3.5 hours later, the reaction mixture is cooled to ambient temperature and quenched with hexane (250 mL) to form a white slurry immediately. The solid is isolated by filtration and all volatile species are removed under vacuum (0.5 mmHg) at 60° C. overnight. The remaining solid is then re-dissolved in $CHCl_3$ and the solution is passed through a column of ion exchange resin to remove catalyst residues. The purified solution is collected and $CHCl_3$ is removed under vacuum at 50° C. overnight, which should yield a white powder (14.2 g). $^{13}C$ NMR experiment should reveal that the product has a molar ratio of 55 (5-R-norbornene): 45 (tert-butyl acrylate). GPC analysis should reveal a unimodal pattern: Mw 25000, Mn 20000, Mw/Mn 1.25.

EXAMPLE 9

Utilizing a neutral metal-pair complex to prepare a copolymer of ethylene and methyl acrylate, according to the method of the present invention. Methyl acrylate (1 mL) and toluene (3 mL) are charged to the glass liner of a steel pressure vessel (8 mL capacity) equipped with a mechanical stirrer. The pressure vessel is sealed and heated to 50° C. Ethylene pressure (350 psig) is introduced. Neutral Metal-Pair Complex IX (8 μmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 4 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. $^1$H NMR should reveal that the product is a copolymer with a molar ratio of 80 (ethylene): 20 (methyl acrylate). GPC analysis should reveal a unimodal pattern: Mw 80000, Mn 50500, Mw/Mn 1.6.

EXAMPLE 10

Utilizing a neutral metal-pair complex to prepare a copolymer of norbornene and methyl acrylate, according to the method of the present invention. A 100 mL serum bottle is charged with toluene (20 mL), norbornene (1.70 g, 18 mmol, pre-dissolved in toluene, 86 wt %), methyl acrylate (1.0 g, 12 mmol) and sealed with a rubber septum. A solution of Neutral Metal-Pair Complex I (0.2 μmol) in $CH_2Cl_2$ is added by syringe at 50° C. The reaction mixture is vigorously stirred at 50° C. 5 hours later, the reaction mixture is cooled to ambient temperature and quenched with methanol (200 mL) to form a pale yellow slurry instantaneously. The solid is isolated by filtration, washed with fresh methanol (3×25 mL), and dried under vacuum at 60° C. overnight, which should yield a pale yellow solid (2.4 g). NMR analysis should reveal that the product has a molar ratio of 72 (norbornene): 28 (methyl acrylate). GPC analysis should reveal a unimodal pattern: Mw 60000, Mn 40000, Mw/Mn 1.25.

EXAMPLE 11

Utilizing a neutral metal-pair complex to prepare a copolymer of ethylene and norbornene, according to the method of the present invention. Norbornene (2 mL of a 79 wt % solution in toluene) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Neutral Metal-Pair Complex II (8 μmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 2 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. $^1$H NMR should reveal that the product is a copolymer with a molar ratio of 55 (ethylene): 45 (norbornene). GPC analysis should reveal a unimodal pattern: Mw 150000, Mn 80000, Mw/Mn 1.9.

EXAMPLE 12

Utilizing a catalytic neutral metal-pair complex to prepare a terpolymer of norbornene, 1-octene and methyl acrylate, according to the method of the present invention. A 100-mL serum bottle is charged with norbornene (12 mmol, pre-dissolved in toluene, 79 wt %), methyl acrylate (12 mmol), 1-octene (30 mmol) and toluene (20 mL), and sealed with a rubber septum. A solution of Neutral Metal-Pair Complex III (0.34 μmol) in $CH_2Cl_2$ is added by syringe at 50° C. The reaction mixture is stirred at 50° C. 4 hours later, the reaction mixture is cooled to ambient temperature and methanol (250 mL). The solid is isolated by filtration, washed with fresh methanol (3×25 mL) and dried under vacuum at 70 deg C. overnight, which should yield a white solid (2.5 g). NMR analysis should reveal that the product has a molar ratio of 15 (norbornene): 30 (1-octene): 55 (methyl acrylate). GPC experiment should reveal a unimodal pattern: Mw 70000, Mn 43750, Mw/Mn 1.6.

EXAMPLE 13

Utilizing a neutral metal-pair complex to prepare a copolymer of ethylene and methyl methacrylate, according to the method of the present invention. Methyl methacrylate (1 mL) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Neutral Metal-Pair Complex IV (8 μmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 4 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. $^1$H NMR should reveal that the product is a copolymer with a molar ratio of 90 (ethylene): 10 (methyl methacrylate). GPC analysis should reveal a unimodal pattern: Mw 25000, Mn 15000, Mw/Mn 1.7.

EXAMPLE 14

Utilizing a neutral metal-pair complex to prepare a copolymer of ethylene and styrene, according to the method of the present invention. Styrene (1 mL) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Neutral Metal-Pair Complex V (8 μmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 4 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. $^1$H NMR should reveal that the product is a copolymer with a molar ratio of 60 (ethylene): 40 (styrene). GPC analysis should reveal a unimodal pattern: Mw 95000, Mn 60000, Mw/Mn 1.6.

We claim:

1. A catalytic composition comprising a neutral metal-pair complex, comprising a first metal atom, $M^1$, and a second metal atom, $M^2$, having a through-space internuclear distance of at least 1.5 Angstroms and no more than 20 Angstroms; wherein said neutral metal-pair complex is according to formula I,

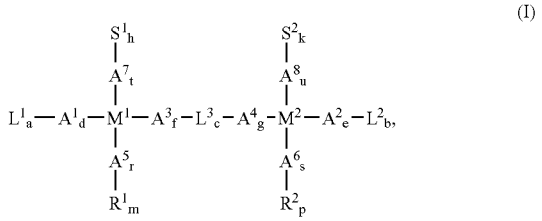

(I)

wherein:

$L^1$ is a set of first ligands;

$L^2$ is a set of second ligands;

$L^3$ is a set of bridging moieties;

$R^1$ is a set of first anionic hydrocarbyl containing radicals;

$R^2$ is a set of second anionic hydrocarbyl containing radicals;

$S^1$ is a set of first labile ligands;

$S^2$ is a set of second labile ligands;

$A^1$-$A^8$ are sets of coordination bonds;

a, b, h, k, m, and p are selected from 0 and 1;

c equals 1;

$1 \leq m+p \leq 2$;

the sum d +f+r+t=4, 5, or 6;

and the sum e +g+s+u=4, 5, or 6;

wherein at least one of $R^1$ and $R^2$ is an addition polymer selected from Poly[(polar olefin)-(non-polar olefin)] and a poly(polar olefin):

with the proviso that (i) when the sum d+f+r+t=4, $M^1$ is selected from nickel, palladium, copper, iron, cobalt, rhodium, chromium, and manganese; d, r, and t are selected from 0, 1, 2, and 3; and f is selected from 1, 2, 3, and 4; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 5$; $1 \leq r+s \leq 5$; $0 \leq t+u \leq 5$; $2 \leq f+g \leq 7$, and, when m+p=2, $R^1$ and $R^2$ are different;

when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 6$; $1 \leq r+s \leq 6$; $0 \leq t+u \leq 6$ and $2 \leq f+g \leq 8$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 7$; $1 \leq r+s \leq 7$; $0 \leq t+u \leq 7$; and $2 \leq f+g9$;

(ii) when the sum d+f+r+t=5;

$M^1$ is selected from iron, cobalt, ruthenium, rhodium, chromium, and manganese; d, r, and t are selected from 0, 1, 2, 3, and 4; f is selected from 1, 2, 3, 4, and 5; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 6$; $1 \leq r+s \leq 6$; $0 \leq t+u \leq 6$; and $2 \leq f+g \leq 8$;

when the sum e+g+s+u=5, $M^2$ is selected from iron, cobalt, ruthenium, rhodium, chromium, and manganese; e, s, and u are selected from 0,1,2,3, and 4; g is selected from 1,2,3,4, and 5; $0 \leq d+e \leq 7$; $1 \leq r+s \leq 7$; $0 \leq t+u \leq 7$; and $2 \leq f+g \leq 9$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0 \leq d+e \leq 8$; $1 \leq r+s \leq 8$; $0 \leq t+u \leq 8$; and $2 \leq f+g \leq 10$ and (iii) when the sum d+f+r+t=6;

$M^1$ is selected from copper, iron, cobalt, ruthenium, rhodium, chromium, and manganese; d, r, and t are selected from 0, 1, 2, 3, 4, and 5; f is selected from 1, 2, 3, 4, 5, and 6; and when the sum e+g+s+u=4, $M^2$ is selected from nickel, palladium, copper, iron, cobalt, rhodium, chromium, and manganese; e, s, and u are selected from 0, 1, 2, and 3; g is selected from 1, 2, 3, and 4; $0 \leq d+e \leq 7$; $1 \leq r+s \leq 7$; $0 \leq t+u \leq 7$; and $2 \leq f+g \leq 9$;

when the sum e+g+s+u=5, $M^2$ is selected from iron, cobalt, ruthenium, rhodium, chromium, and manganese; e, s, and u are selected from 0, 1, 2, 3, and 4; g is selected from 1, 2, 3, 4, and 5; $0 \leq d+e \leq 8$; $1 \leq r+s \leq 8$; $0 \leq t+u \leq 8$; and $2 \leq f+g \leq 10$; or when the sum e+g+s+u=6, $M^2$ is selected from copper, iron, cobalt, ruthenium, rhodium, chromium, and manganese; e, s, and u are selected from 0, 1, 2, 3, 4, and 5; g is selected from 1, 2, 3, 4, 5, and 6; $0d+e \leq 9$; $1 \leq r+s \leq 9$; $0 \leq t+u \leq 9$; and $2 \leq f+g \leq 11$.

2. The catalytic composition of claim 1, wherein said through-space internuclear distance is at least 2 Angstroms and no more than 10 Angstroms.

3. The catalytic composition of claim 1, wherein at least one of $R^1$ and $R^2$ is a poly[(polar olefin)-(non-polar olefin)] addition polymer, wherein the molar ratio of the polar olefinic monomers to non-polar olefinic monomers present as polymerized units in the poly[(polar olefin)-(non-polar olefin)] addition polymer is at least 0.05:99.95.

4. A method for preparing an addition polymer comprising:

(a) combining:

(i) a catalytic composition according to claim 1, and (ii) an ethylenically unsaturated monomer; and (b) polymerizing said ethylenically unsaturated monomer in the presence of said catalytic composition to form said addition polymer;

wherein the addition polymer is selected from poly[(polar olefin)-(non-polar olefin)] and a poly(polar olefin).

5. The method of claim 4, wherein said $M^1$ and said $M^2$ of said metal atom pair exhibit cooperativity during said polymerization.

6. The method of claim 4, wherein said addition polymer is a poly[(polar olefin)-(non-polar olefin)] having a combined molar percentage of polar olefinic monomers and non-polar olefinic monomers, present as polymerized units, of at least 70 mole-% to 100 mole-% (based upon the total moles of all polar olefinic monomers and non-polar olefinic monomers, present as polymerized units.

7. The method of claim 4, wherein said addition polymer comprises, as polymerized units, at least one (meth)acrylate monomer having a molar ratio to all said ethylenically unsaturated monomers, present as polymerized units, of at least 0.05:99.95 to 100:0.

8. The method of claim 4, wherein said addition polymer comprises, as polymerized units, at least one cyclic olefin monomer having a molar ratio to all said ethylenically unsaturated monomers, present as polymerized units, of at least 0.05:99.95 to 100:0.

9. The method of claim 4, wherein:
when said sum $d+f+r+t=4$ and said sum $e+g+s+u=4$,
said bridging moiety comprises no more than one atom selected from oxygen and sulfur bonded directly to a metal atom of a metal atom pair.

10. The method of claim 4, wherein said step of combining further comprises a neutral co-catalyst.

* * * * *